(12) United States Patent
Recoli et al.

(10) Patent No.: US 7,041,785 B1
(45) Date of Patent: May 9, 2006

(54) B$_1$-BRADYKININ RECEPTOR ANTAGONISTS AND USE THEREOF

(75) Inventors: Domenico Recoli, Magog (CA);
Gerard E. Plante, Sherbrooke (CA);
Fernand Gobeil, Chomedey (CA);
Witold A. Neugebauer, Ottawa (CA);
Adriana Zucollo, Buenos Aires (AR);
Orlando L. Catanzaro, Buenos Aires (AR)

(73) Assignee: Université de Sherbrooke, Sherbrooke (CA)

(*) Notice: Subject to any disclaimer, the term of this patent is extended or adjusted under 35 U.S.C. 154(b) by 0 days.

(21) Appl. No.: 09/242,751

(22) PCT Filed: Aug. 14, 1997

(86) PCT No.: PCT/CA97/00582

§ 371 (c)(1),
(2), (4) Date: Aug. 9, 1999

(87) PCT Pub. No.: WO98/07746

PCT Pub. Date: Feb. 26, 1998

Related U.S. Application Data

(60) Provisional application No. 60/023,971, filed on Aug. 19, 1996.

(51) Int. Cl.
*A61K 38/00* (2006.01)
*A61K 49/00* (2006.01)

(52) U.S. Cl. .................. 530/314; 514/2; 514/15; 530/327; 530/328; 424/9.1

(58) Field of Classification Search ............ 530/314, 530/327, 328; 514/15, 2; 424/9.1
See application file for complete search history.

(56) References Cited

U.S. PATENT DOCUMENTS

| | | | |
|---|---|---|---|
| 5,552,383 A | 9/1996 | Kyle et al. | |
| 5,750,506 A | 5/1998 | Goodfellow et al. | |
| 5,834,431 A * | 11/1998 | Stewart et al. | 514/15 |
| 6,075,120 A | 6/2000 | Cheronis et al. | |
| 6,288,036 B1 | 9/2001 | Kyle et al. | |

FOREIGN PATENT DOCUMENTS

| WO | WO 92 18156 | 10/1992 |
|---|---|---|

OTHER PUBLICATIONS

IUPAC-IUB Joint Commission on Biochemical Nomenclature (JCBN), Nomenclature and symbolism for amino acids and pepptides, Eur. J. Biochem., 1983, 138:9-37.
Alvarez et al., 1992, Clinical Science 82:513-519.
Catanzaro et al., 1994, Brazilian J. Med. Biol. Res. 27:2043-2047.
Chakir et al., 1995, Medecine/Sciences 11 (suppl.2):15.
Chakir et al., 1995, Eur. J. Pharmacol 285:11.
Cooke, A., 1990, Curr. Top. Microbiol. Immunol. 164:125-142.
Davis et al., 1994, Brazilian J. Med. Biol. Res 27:1793-1802.
Davis et al., 1994, Br. J. Pharmacol 113:63-68.
Drapeau et al., 1988, Methods in Enzymology 163:263-272.
Drapeau et al., 1993, J. Pharmacol. Exp. Ther. 266:192-198.
Dray et al., 1993, Trends in Neurosci. 16:99-104.
Erdös et al., 1986, Hypertension 8:34-37.
Ferreira et al., 1967, Brazilian J. Pharmac. Chemother. 30:417-424.
Furchgott et al., 1953, J. Pharmacol Exp. Ther. 108:124-143.
Gaudreau et al., 1981, Can. J. Physiol. Pharmacol. 59:371-379.
Gobeil et al., 1996, Can. J. Physiol. Pharmacol. 74:137-144.
Gobeil et al., 1996, Hypertension 28:833-839.
Gobeil et al., 1996, Br. J. Pharmacol. 188:289-294.
Green et al., 1982, Analytical Biochemistry 126:131-138.
Griesbacher et al., 1992, Br. J. Pharmacol 108:356-360.
Hall J.M., 1992, Pharmac. Ther. 56:131-190.
Harvey et al., 1990, Diabetes 39:299-304.
Hilgenfeldt et al., 1995, Analytical Biochemistry 228:35-41.
Hock et al., 1991, Br. J. Pharmacol. 102:769-773.
Kato et al., 1988, FEBS Lett. 232:252-254.
Kolb-Bachofen et al., 1988, Diabetes 37:21-27.
Lévesque et al., 1995, Immunopharmacology 29:141-147.
Lowry et al., 1951, J. Biol. Chem. 193:265-275.
Mandrup-Poulsen et al., 1985, Allergy 40:424-429.
Maier et al., 1988, FEBS Lett. 232:395-398.
Marceau, François, 1995, Immunopharmacology 30:1-26.
Menke et al., 1994, J. Biol. Chem. 269:21583-21586.

(Continued)

*Primary Examiner*—Jon Weber
*Assistant Examiner*—Chih-Min Kam
(74) *Attorney, Agent, or Firm*—Rick Matos; Innovar, L.L.C.

(57) ABSTRACT

The present invention relates to novel antagonists to a $B_1$-bradykinin ($B_1$-BK) receptor which have a good affinity and selectivity therefor, some of which being at least partially resistant to enzymatic degradation. The synthesis of the $B_1$ receptors is induced during inflammation. Symptoms associated with inflammation (elevated hydrostatic pressure and plasma leakage or extravasation) have been observed in diabetic animal models (streptozotocin-induced diabetes (STZ)) as well as in spontaneously hypertensive rats (SHR). The present inventors confirm the presence of $B_1$-BK receptors in these two models. $B_1$-BK antagonists abolished the vasocontraction induced by $B_1$-BK in SHR and STZ, and reduced the glycemia of diabetic animals to normal levels. The present $B_1$-antagonists are useful for treating any condition wherein $B_1$-receptor is expressed, particularly during inflammation, and more particularly wherein $B_1$-receptor expression results in diabetic vasculopathy, other diabetic symptoms associated with an insulitis and a post-capillary resistance building as a consequence of the presence of a $B_1$-receptor.

12 Claims, 2 Drawing Sheets

OTHER PUBLICATIONS

Plante et al., 1992, J. Clin. Invest. 89:2030-2032.
Rang H.P., 1964, Brit. J. Pharmacol. 22:356-365.
Regoli et al., 1977, Can. J. Physiol. Pharmacol 55:855-867.
Regoli et al., 1986, Eur. J. Pharmacol. 127:219-224.
Regoli et al., 1994, Life Sciences 55:735-749.
Regoli et al., 1990, Trends in Pharmacol. Sci. 11:156-161.
Regoli et al., 1980, Can. J. Physiol. Pharmacol. 32:1-46.
Regoli et al., 1996, Immunopharmacology 33:116-122.
Rhaleb et al., 1992, Life Sciences 51:125-129.
Rhaleb et al., 1991, Hypertension 17:107-115.
Rhaleb et al., 1990, Br. J. Pharmacol. 99:445-448.
Schild et al., 1947, Brit. J. Pharmacol 2:189-206.
Stewart et al., 1991, in: Bradykinin Antagonists: Basic and Clinical Research, R.M. Burch Ed. Marcel Dikker, New York, 51-60.
Wirth et al., 1991, Eur. J. Pharmacol. 205:217-218.
Zuccollo et al., 1996, Can. J. Physiol. Pharmacol 74:586-589.
Allogho et al., 1995, Can. J. Phys. Pharmacol. 73:1759-1764.
Gobeil et al., 1997, Can. J. Physiol. Pharmacol. 75:591-595.
Mouna Chakir, Petro D'Orléans-Juste, Gérard E. Plante, "Neutral endopeptidase inhibition, a new approach in the exploration of diabetic vasculopathy in rats," *European Journal of Pharmacology* 285 (1995) 11-18.
James Togo, Ronald M. Burch, Christopher J. DeHaas, Jane R. Connor and Larry R. Steranka, "D-Phe$^7$-Substituted Peptide Bradykinin Antagonists are not Substrates for Kininase II," *Peptides*, vol. 10 (1989) 109-112.
S. B. Vila, V. A. Peluffo, C. Alvarado, J. C. Cresto, A. Zuccollo, O. L. Catanzaro, "The Kallikrein-kinin System in Early State of Diabetes," *Recent Progress on Kinins*, pp. 304-310.
Ferreira et al. (*Neuropharmacology* (2001), 41(8), 1006-1012), abstract.
Ferreira et al. (*Regul. Pept.* (2000), 89(1-3), 29-35), abstract.
Abraham (*Agents Actions* Suppl. (1992), 38 (Pt. 3), 439-449), abstract.
Couture et al. (*Eur. J. Pharmacol.* (2001), 429(1-3), 161-176), abstract.
Zuccollo et al. (*Immunopharmacology* (1999), 45(1-3), 69-74), abstract.

* cited by examiner

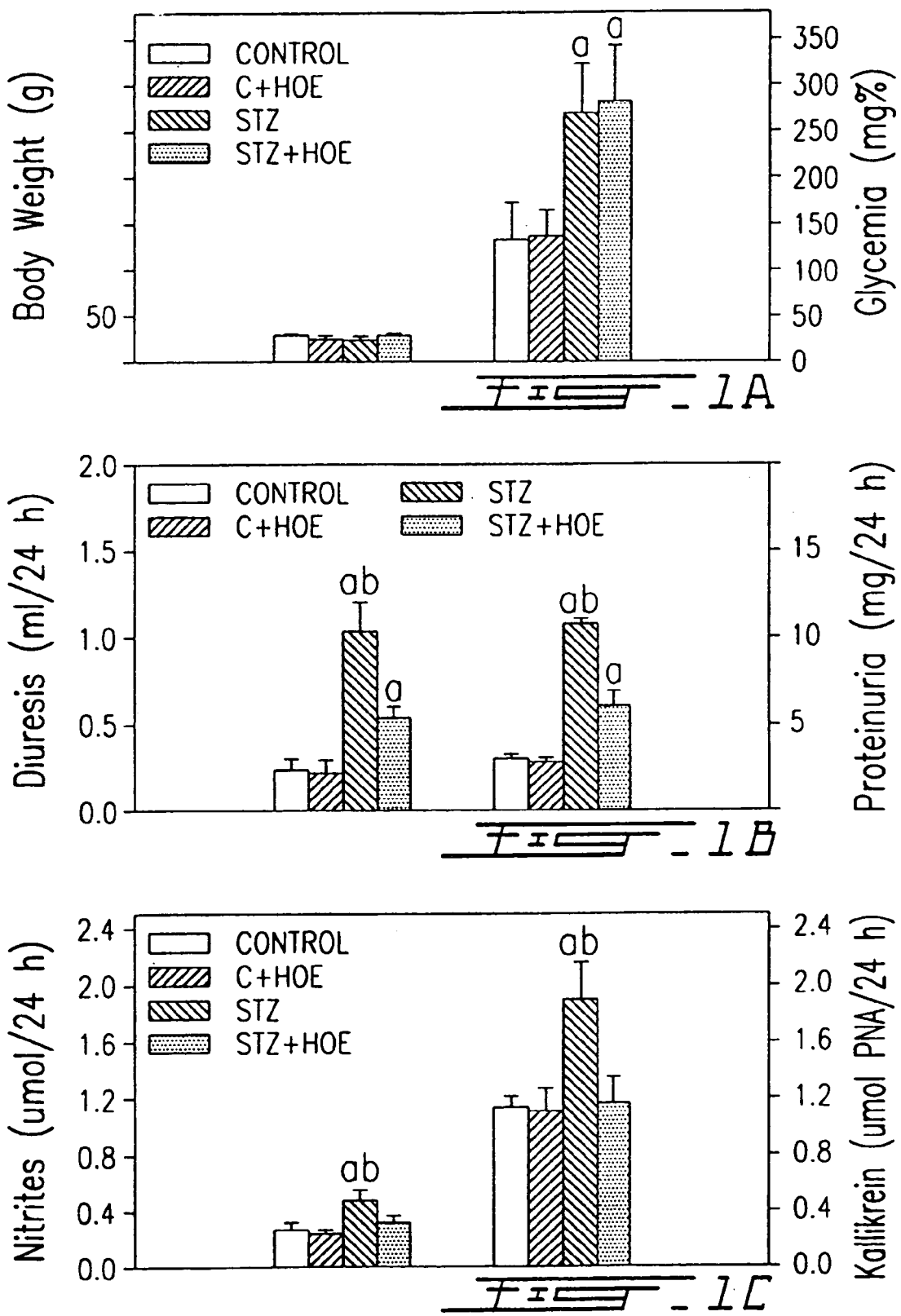

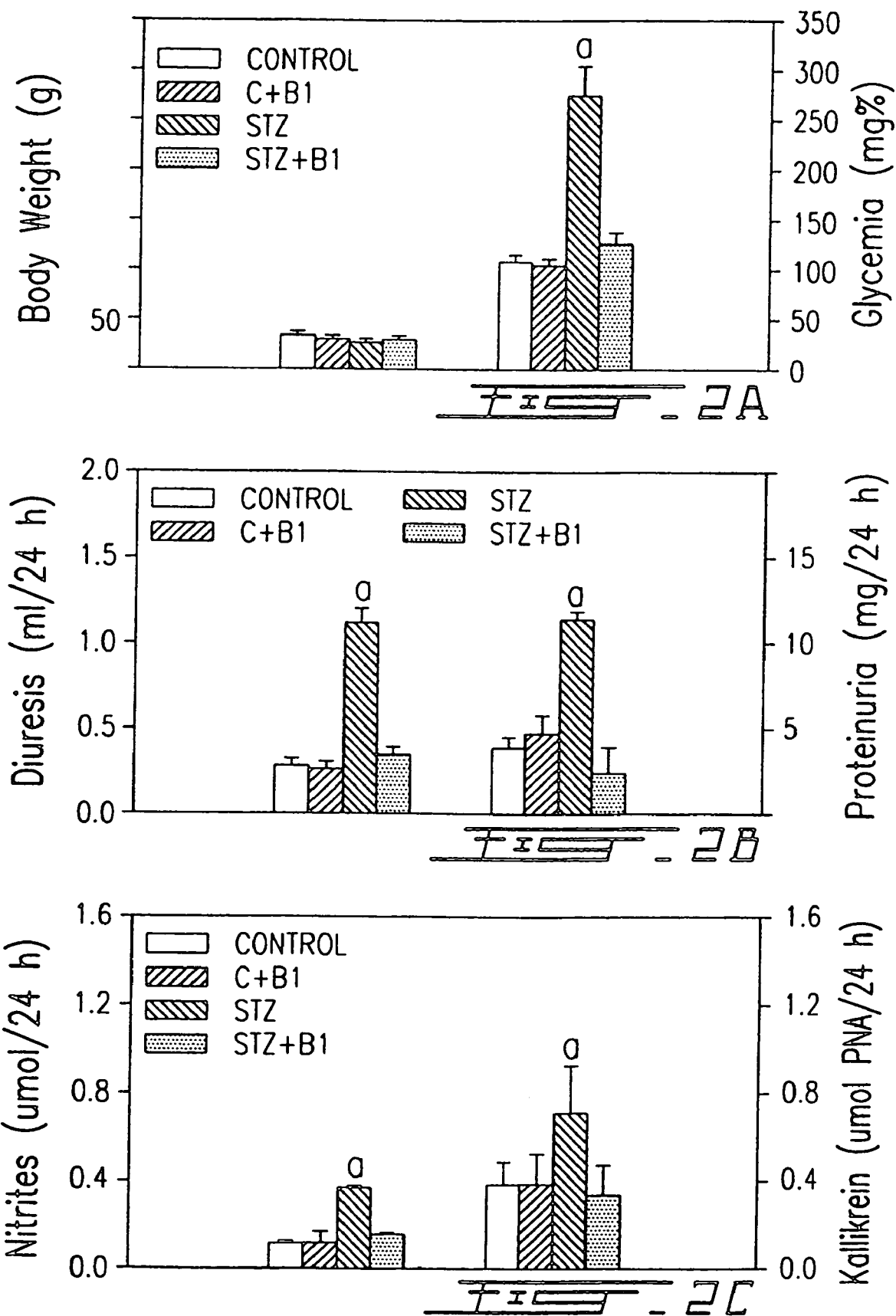

B₁-BRADYKININ RECEPTOR ANTAGONISTS AND USE THEREOF

This application is a 371 of PCT/CA97/00582, filed Aug. 14, 1997, which claims benefit of U.S. Provisional Application 60/023,971, filed Aug. 19, 1996.

FIELD OF THE INVENTION

This invention relates to $B_1$-antagonists that have a good affinity and selectivity for a $B_1$-receptor; a subset thereof at least partially resistant to enzymatic degradation.

BACKGROUND OF THE INVENTION

The synthesis of $B_1$ bradykinin ($B_1$-BK) receptor is induced during inflammation in blood vessel muscular layers. This receptor is not present in normal conditions. This is in contrast with the $B_2$-BK receptor which is normally present on many cell types or tissues. $B_1$ receptor is present in the muscular layer of blood vessels and appears to be a factor involved in the vasoconstriction, the enhanced hydrostatic pressure and plasma leakage observed in an animal model of spontaneous hypertension (SHR) and in streptozotocin-induced diabetic rat model (STZ).

Many patent publications describe antagonists of bradykinin receptors. However, these antagonists all have an activity towards $B_2$-receptors. If, amongst these agonists, one may find antagonists that may be converted into $B_1$-antagonists by the action of carboxypeptidases, it remains that their verified activity towards $B_2$-receptors indicates that such antagonists would not be selective for $B_1$-receptors.

Recent reports point to an important role of kinin $B_1$ receptors in physiopathology. Dray and Perkins[1] have reviewed the possible implication of $B_1$ receptors in various inflammatory states, tissue reactions and hyperalgesia, particularly the chronic phases of these experimental diseases. This has been further supported by some recent findings from Davis and coworkers[2] in inflammatory hyperalgesia in the rat. Using $B_1$ receptor antagonists, Alvarez et al.[3] have suggested that $B_1$ receptors may be present in spontaneous hypertensive rats whereas Chakir et al.[4] and Zuccollo et al.[5], have obtained strong evidence that $B_1$ receptors may play a relevant role in streptozotocin-induced diabetes in rat and mouse models, respectively. It thus appears that $B_1$ receptors are formed de novo and take part in the induction and/or the maintenance of pathological states. Or, as pointed out by Marceau[6], "it is conceivable that $B_1$ receptors can amplify the responses of injured tissues to kinins and, in some cases, take the relay of $B_2$ receptors in chronic pathologies". $B_1$ receptor antagonists have been discovered in the late seventies[7,8] but no substantial progress has been made in this area, despite the evidence of their usefulness in basic pharmacology and in various experimental pathologies.

We air ady demonstrated that capillary permeability was augumented in str ptozocin (STZ) diabetic rat model[49]. The vascular BK receptors of the portal veins of these animals have been shown to present enhanced contractibility and capillary permeability in response to $B_1$-agonist desArg⁹BK, when compared to normal animals. This effect was abolished by $B_1$-antagonist Lys(Leu⁸)desArg⁹BK while the $B_2$-antagonist HOE140 had no effect thereon. A similar increased sensitivity to desArg⁹BK was observed in untreated SHR animals, prior to the establishment of hypertension, which was reversed by the same $B_1$-antagonist. Even if these results indicate that $B_1$-receptor is a target for a drug-preventive approach to diabetic or hypertensive vasculopathy, clinical testing becomes possible in as much as $B_1$-antagonists capable of resisting to a very rapid enzymatic degradation are obtained. Substitutions in the natural $B_1$-agonist desArg⁹-BK at amino acid residue proline have provided antagonists resistant to ACE degradation[23]. Further protection against amino peptidases is provided by adding non-hydrolysable amino acid residues at the N-terminal end. However, modifications at both residue 7 and N-terminal end also resulted in a loss of affinity for $B_1$-receptor and even showed antagonistic activity towards $B_2$-receptor.

Commercially available bradykinin antagonists also exist: D-Arg(Hyp³,Thi⁵,D-Tic⁷,Oic⁸)desArg⁹BK (S0765), (Hyp³, Thi⁵,D-TiC⁷,OiC⁸)desArg⁹BK (S1629) both developed by Hoechst, D-Arg(Hyp³,D-Hyp⁷(transpropyl),Oic⁸) desArg⁹BK (NPC18565) and D-Arg(Hyp³,D-Hyp⁷(trans thiophenyl), Oic⁸)desArg⁹BK (NPC18828), both developed by Scios Inc., are antagonists completely resistant to ACE degradation. However, none of them are selective for $B_1$-receptor when tested in model tissues.

From the foregoing, it is apparent that there is a need for $B_1$-antagonists which would be at least partially resistant to proteolytic enzymes, while the affinity and selectivity thereof for a $B_1$-receptor would be preserved.

STATEMENT OF THE INVENTION

It is an object of the present invention to provide $B_1$-antagonists which have an acceptable affinity and selectivity for a $B_1$-receptor, some of which are at least partially resistant to proteolytic degradation. These antagonists are used as therapeutic agents for treating any condition wherein a $B_1$-receptor mediated response is expressed.

Pharmaceutical compositions comprising these $B_1$-antagonists and a pharmaceutically acceptable carrier are also an object of the invention.

It is further another object of the invention to provide methods of treating a subject affected by a condition wherein a $B_1$-receptor mediated response is building. Such a condition is particularly an inflammatory condition, more particularly a diabetic vasculopathy, other diabetic symptoms associated with an insulitis or a post-capillary resistance consequent to the presence of a $B_1$-receptor.

It is also another object of this invention to provide a new use for the commercially available non-selective $B_1$ antagonists as selective $B_1$-antagonists in humans.

DESCRIPTION OF THE INVENTION

The present inventors have focused their attention on the $B_1$-BK blockade and the therapeutic effects of that blockade. Novel $B_1$-BK receptor antagonists are provided. These antagonists are selective to $B_1$-BK receptors, and some of them are partially or totally resistant to enzymatic degradation.

Previous studies with the $B_1$ antagonist Lys(Leu⁸) desArg⁹BK completely abolished the contraction induced by a $B_1$ agonist desArg⁹-BK in perfused tissues expressing this receptor as well as in an animal model of spontaneous hypertension (SHR) and in streptozotocin-induced diabetic rat model (STZ). It is contemplated that the $B_1$-antagonists of the present invention have the same effect on these tissues and animal models as the previous $B_1$-antagonist used for these experiments.

To facilitate understanding of the design of the $B_1$-antagonists of this invention, the structure of bradykinin (BK), kallidin (KD) and their naturally encountered C-terminal truncated forms are given below:

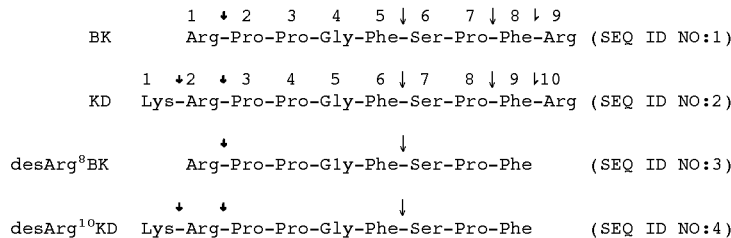

The vertical arrows illustrate the sites of proteolytic cleavage by a carboxy peptidase (↓), ACE (↓) and an aminopeptidase (↓). In order to uniformize the nomenclature of the peptides, kallidin and its desArg$^9$ metabolite will be named with reference to BK as (Lys) BK and (Lys) des-Arg$^9$BK. All substitutions and additions of amino acids in the N-terminal are designated as follows: substitutions are given within brackets by naming substituents and their amino acid position, while additions in the N-terminal precede the opening bracket without numerotation. For example, addition of a N-terminal lysine residue and substitution of a leucin for the phenylalanine at position 8 of desArg$^9$bradykinin is designated Lys(Leu$^8$)desArg$^9$BK (SEQ ID NO. 6).

LysBK and BK are agonists of $B_2$-receptors, normally present at the membrane surface of numerous cells. C-terminal truncated metabolites (Lys)desArg$^9$BK (SEQ ID NO. 4) and desArg$^9$BK (SEQ ID NO. 3) are agonists of a $B_1$-receptor, not present on normal cells, but synthesized de novo during inflammation. $B_1$-antagonists of the present invention are peptide analogs of desArg$^9$BK.

The present invention is the result of a study that was undertaken to search for new peptidic $B_1$ receptor antagonists, starting with the most active known structure Lys(Leu$^8$)desArg$^9$BK[5] and trying to improve it. Changes were made at the N-terminal end to find the most suitable group that maintains affinity and protects from degradation by aminopeptidases and in positions 7 and 8 to improve affinity and resistance to kininase II or ACE (EC 3.4.15.1), the enzyme that plays a major role in the inactivation of the kinins and their desArg$^9$-metabolites[8,9]. New compounds were prepared and tested in several isolated organs to provide precise pharmacologic profiles and assess affinity and selectivity for the $B_1$ receptor.

This invention will be described hereinbelow by way of specific Examples, Tables and Figures, which purpose is to support and illustrate the invention rather thna to limit its scope.

BRIEF DESCRIPTION OF FIGURES

FIGS. 1a), 1b) and 1c) represent the effect of HOE140 (a selective $B_2$ bradykinin receptor antagonist) on glycemia, proteinuria and kallikrein excretion, respectively, in control mice and streptozotocin-induced diabetes type I in mice.

FIGS. 2a), 2b) and 2c) represent the effect of (Leu$^8$)desArg$^9$BK (SEQ ID NO. 5) (a selective $B_1$ bradykinin receptor antagonist) on glycemia, proteinuria and kallikrein excretion, respectively, in control mice and streptozotocin-induced diabetes type I in mice.

EXAMPLE 1

Design and Activity of desArg$^9$BK Analogs

Peptide Synthesis

All peptides were synthesized with an Applied Biosystems 430 A peptide synthesizer using Merrifield type resins with the first amino acid attached. Amino acids were activated by dicyclohexylcarbodiimide 1-hydroxybenzotriazole (Peptides International, Louisville, Ky.) on 1-methyl-2-pyrrolidinone. Peptides were cleaved from the resins with anhydrous HF in the presence of appropriate scavengers. The resulting peptides were purified by medium pressure reversed-phase ($C_{18}$) chromatography and if necessary by HPLC. Peptide purity was assessed by analytical HPLC and identity confirmed by Ion spray mass spectrometry (VG Quattro, Manchester, U.K.).

Bioassays

Tissues were taken from New Zealand white rabbits (1.5–2.5 kg) and Dunken Hartley guinea pigs (250–350 g) of either sex, killed by stunning and exsanguination. Umbilical cords were taken from healthy women 22–40 years old after spontaneous delivery at term. The rabbit jugular vein (RbJV), the guinea pig ileum (GPI), two preparations containing $B_2$ receptors, the rabbit aorta (RbA) ($B_1$ receptor) and the human umbilical vein (HUV), a mixed preparation containing both $B_1$ and $B_2$ receptors[10], were used. Helical strips of RbJV treated with 1 µmol/L of captopril to avoid peptide degradation by the angiotensin-converting enzyme (ACE), alias kininase II were prepared according to Gaudreau et al.[11] Helical strips of RbA devoid of endothelium were prepared according to Furchgott and Bhadrakom[12]. Longitudinal segments of GPI were prepared with the procedure described by Rang[13]. Helical strips of HUV were prepared according to Gobeil et al.[10]. The tissues were suspended in 10-ml organ baths containing warm (37EC), oxygenated (95% $O_2$–5% $CO_2$) Krebs solution of the following composition in mmol/L; NaCl: 118.1; KCl: 4.7; $CaCl_2 6H_2O$: 2.5; $KH_2PO_4$: 1.2; $MgSO_4 7H_2O$: 1.18; $NaHCO_3$: 25.0 and D-Glucose: 5.5. The RbA and the HUV were stretched with an initial tension of 2 g, whereas the RbJV and the GPI were loaded with 0.5 g. Changes of tension produced by the various agents were measured with Grass isometric transducers (model FT 03C, Grass Instrument Co., Quincy, Mass.). Myotropic contractions were displayed on a Grass polygraph (model 7D). Before testing the drugs, the tissues were allowed to equilibrate for 60–120 min during which time the tissues were repeatedly washed and the tension readjusted every 15 min.

At the beginning of each experiment, a submaximal dose of bradykinin (BK) (9 nmol/L), was applied repeatedly on the RbJV, the GPI or the HUV to ensure that tissues responded with stable contractions. In the RbA, the $B_1$ preparation whose response has been shown to increase during the incubation in vitro[7], desArg[9]BK (550 nmol/L) was applied 1,3 and 6 h after the equilibration period, in order to monitor the progressive increase of sensitivity of the tissue which generally reaches the maximum after 3–6 h. A similar protocol was used for the HUV.

Repeated applications of a singl and double concentration of BK (on RbJV, GPI and HUV) and of desArg[9]BK (RbA and HUV) were made in the absence and in presence of the various peptides to evaluate their apparent affinities as antagonists, in terms of $pA_2$ ($-\log_{10}$ of the molar concentration of antagonist that reduces the effect of a double concentration of agonist to that of a single one)[14]. The antagonists were applied 10 min before measuring the myotropic effects of either BK (the $B_2$ receptor agonist) or desArg[9]BK (the $B_1$ receptor agonist). Pharmacological assays on the HUV (a mixed $B_1$ and $B_2$ receptor preparation) were done in presence of either HOE140 (400 nmol/L) (a potent $B_2$ receptor antagonist) or Lys(Leu8)des Arg[9]BK (1 μmol/L) (a potent $B_1$ receptor antagonist) (applied 10 min prior to the tested agents) to study the $B_1$ and the $B_2$ receptors, respectively[10]. All kinin antagonists were initially applied to tissues at concentration of 10 μg/mL to measure their potential agonistic activities ($\alpha^E$) in comparison with BK (in the $B_2$ receptor preparations) or desArg[9]BK (in the $B_1$ receptor preparations).

Experimental Protocol for Biochemical Assays

The metabolic stability of various kinin-related peptides was evaluated by incubating the peptide in the presence of purified angiotensin-converting enzyme (ACE) from rabbit lungs (purchased from Sigma, St-Louis, Mo.) dissolved in phosphate buffered saline (PBS) (50 mmol/L, pH 7.5 containing 300 mmoL/L NaCl); the final concentration of enzyme was 45 μg/mL. The experimental protocol for the measurement of ACE activity has been described elsewhere[15,16]. Briefly, 200 μmol/L of peptides (40 μL) were placed in a PBS buffer and incubated for 5 min at 37EC before adding 8.5 μL of ACE (total volume of the reaction medium; 190 μL). Samples were withdrawn at 30 min intervals, immersed in boiling water for 5 min, then cooled on ice and centrifuged (5 min) before proceeding to analysis of peptides by high pressure liquid chromatography (HPLC). Results of ACE metabolism are expressed in percent of kinin degradation following the incubation (30 min) of kinin substrates with the enzyme. In these experimental conditions and at the enzymatic dilution indicated above, naturally-occurring kinins (e.g. BK and desArg[9]BK) were found to be fully metabolised after 30 min[16].

HPLC Analysis of Peptide Digests

Pure peptides and metabolic products were analysed by reverse-phas HPLC on a $C_{18}$ μBondapak column (4.6 mm×25 cm) (Waters) of 10-μm particle size. The peptides and their fragments were eluted at the rate of 2.0 mL/min. with a linear gradient ranging from 5 to 65% of acetonitrile/TFA 0.05%/water over 20 min. at room temperature. The elution positions of these peptides were determined by following the absorbance at 214 nm. For each assay, 50 μL of the reaction medium (treated or not with ACE) were extracted and injected into the column. Concentrations of the peaks products, different from the peaks of the peptide substrate, were estimated using a computer software program (Baseline 810; Waters) that controlled also all the chromatography operations. Isolated metabolites and substrates were collected and identified by Electrospray mass spectrometry (positive mode).

Drugs

The B2 antagonist D-Arg(Hyp[3], Thi[5], D-Tic[7], Oic[8])BK (HOE140), and HOE140 derivatives (D-Arg(Hyp[3], Thi[5], D-Tic[7], Oic[8])desArg[9]BK (S 0765) (SEQ ID NO. 35) and (Hyp[3], Thi[5], D-Tic[7],Oic[8])desArg[9]BK) (S 1629) (SEQ ID NO. 36))[17] were given by Dr. B. Schölkens (Hoechst, Frankfurt, Germany) and two other peptides (D-Arg(Hyp[3], D-Hyp[7] (trans propyl), Oic[8])desArg[9]BK (NPC 18565) (SEQ ID NO. 37) and D-Arg(Hyp[3], D-Hyp[7] (trans thiophenyl), Oic[8])desArg[9]BK) (NPC 18828) (SEQ ID NO. 38)) were supplied by Dr. D. J. Kyle (Scios Inc., Mountain View, Calif.). The peptide AcLys(N-MeAla[6], Leu[8])desArg[9]BK[15] (SEQ ID NO. 25) was donated by Dr. G. Drapeau (Centre de recherche Hotel-Dieu de Quebec, Quebec, Canada). A series of new peptide analogues of Lys(Leu[8])desArg[9]BK (see abbreviated structures in Table 1) were prepared in our laboratory with the procedure described by Drapeau and Regoli[18] and they were analysed as described above. Abbreviations follow the recommendations of the IUPAC-IUB Commission on Biochemical Nomenclature[19]. Other abbreviations are described as follows: Hyp: trans4-hydroxy-L-proline; Thi: p-(2-thienyl)L-alanine; Tic: L-(1,2,3,4-tetrahydroisoquinoline-3carboxylic acid); Qic: L-(3aS, 7aS)-octahydro-indol-2-carboxylic acid; ☐Nal: ☐9-3-(2-naphthyl) alanine: Sar: sarcosine (N-methyl-glycine); ☐Ahx: ☐1-aminohexanoic acid. Captopril was purchased from Squibb Canada (Montreal, Canada). All chemical agents, were obtained from either Bachem CA (Torrance, Calif.) or Novabiochem (La Jolla, Calif.). Concentrated solutions (1 to 5 mg/mL) of peptides and other agents were made in bidistilled and deionized water and kept at −20 C until used.

Results

The results obtained with three series of compounds designed to a) improve antagonistic affinity, b) eliminate residual agonistic activities and c) prevent the degradation of $B_1$ receptor antagonists by ACE, are presented in Table 1, 2 and 3. The first series (Table 1) includes compounds (containing a Hyp residue in position 3), which may derive from the conversion by carboxypeptidases of classical $B_2$ receptor antagonists into C-terminal desArg[9]-fragments. The results, summarized in Table 1, present the pharmacological profile of each compound in terms of affinities ($pA_2$) for the $B_1$ receptor (RbA) and affinities (if any), as well as residual agonistic activities on two $B_2$ receptor subtypes (RbJV, GPI). Percent of degradation (after 30 min of incubation) by ACE is also indicated.

Pharmacological profiles of compounds 1 and 2 are in agreement with those reported by others[7,8] and indicate that the presence of a Lys residue at the N-terminal is favourable for antagonism on the $B_1$ receptor, since Lys(Leu[8])deArg[9]BK is 10 fold more active than (Leu[8])desArg[9]BK. These peptides are rapidly inactivated by ACE. The presence of Hyp residue in position 3 and that of a D-Arg at the N-terminal (two modifications that favour antagonistic affinity on $B_2$ receptors)[20,21,22] bring a loss of the antagonistic affinity on $B_1$ receptors (see compound 4) and eventually evoke some residual agonistic activities, especially on the guinea pig $B_2$ receptor subtype. Most of the changes at the N-terminal neither protect from degradation by ACE nor improve affinity for the rabbit $B_1$ receptor. The desArg[9]-metabolites of $B_2$ receptor antagonists of the first generation (compounds 6 and 7)[20,21] also show low affinity on the $B_1$ receptor and eventually exert weak antagonism on the $B_2$ receptor of the RbJV. These compounds are expected to be resistant to ACE degradation because of the presence of a D-residue in position 7, which has been shown to protect bradykinin analogues from ACE[23].

Results obtained with compounds in which Pro in position 7 was replaced by D-Tic are summarized in Table 2. Thus, D-Tic in position 7 prevents the proteolytic activity of ACE, and also reduces affinity for the $B_1$ receptor markedly. Furthermore, two compounds (# 17 of Table 2 and #26 of Table 3) were tested as inhibitors of ACE and were found (at concentrations up to $10^{-4}$ M) not to interact with the degradation of desArg$^9$BK by the enzyme (C. Filteau and F. Gobeil, personal communication). To restore antagonistic affinity, various residues (Sar, Lys, AcLys or D-Arg) were added at the N-terminal of the (D-Tic$^7$, Leu$^8$)desArg$^9$BK (SEQ ID NO. 12) (compound 8). An increase of antagonistic affinity by 0.8 log unit is obtained with the inclusion of a D-Arg (see compound 12). Moreover, the two compounds containing Lys (compounds 10 and 11) act as partial agonists in the $B_2$ receptor preparations (especially on the GPI); these myogenic effects can not be abolished by HOE140 (10 µg/mL), a potent $B_2$ receptor antagonist (not shown). For this series of compounds, the most suitable chemical modifications appear to be D-Arg at the N-terminal and Ile position 8 (compound 13). In fact, D-Arg(D-Tic$^7$, Ile$^8$) desArg$^9$BK (SEQ ID NO. 17) is an antagonist on the $B_1$ receptor showing a $pA_2$ value of 6.97 with no agonistic activity on the $B_2$ receptor and negligible degradation by ACE. Replacement of the D-Tic stereoisomer (compound 14) in position 7 causes a diminution of the antagonistic potency ($pA_2<5.04$) on the $B_1$ receptor as well as regaining its susceptibility of being metabolized by ACE. The same results have been obtained when the D-Tic residue in position 7 has been replaced by a smaller residue such as an Ala (see compound 15). The presence of a Hyp residue in position 3 does not seem to play any particular role (see compounds 16, 17).

In a third series of compounds, presented in Table 3, Pro in position 7 was substituted by a βNal and the N-terminal was prolonged either with a single residue or with a short peptidic chain, containing a Tyr residue for iodine labelling. In this series, the residue of choice for the N-terminal appears to be AcLys (see compounds 18, 19), since D-Arg, D-Lys or Sar, although suitable for protection from aminopeptidases, reduce antagonistic affinity for the $B_1$ receptor to an extent of 0.5 to 1 log unit. Moreover, compounds 19, 22, 23, 25 and 26 (containing Ile in position 8) are partial agonists on the GPI. Again, these contractile effects are not be prevented by HOE140 (10 µg/mL), and thus, should be considered as non specific. As to position 8, Leu has the advantage over Ile in eliminating partial agonistic activities on the GPI (and RJV) as well as conferring better protection against ACE hydrolysis (see Table 3). However, this latter substitution causes a slight reduction of antagonism potency compared to those containing an Ile (see Table 3). The AcLys(D-βNal$^7$,Ile$^8$)desArg$^9$BK (SEQ ID NO. 23) (compound 19) represents the most potent $B_1$ receptor antagonist ($pA_2$ 8.40±0.12) with little residual agonistic effect on the GPI ($\alpha^E$ 0.38) and is partially metabolized by ACE in our experimental conditions. Furthermore, electrospray mass spectrometry analysis of the composition of the degradation mixture of the AcLys(D-βNal$^7$, Ile$^8$)desArg$^9$BK is in agreement with the proteolysis pattern of desArg$^9$-peptides by ACE and led to the identification of C-terminal tetrapeptidyl fragments (not shown). Complete protection from ACE is obtained by replacing Ser in position 6 with an N-MeAla but this is accompanied by a marked loss of $B_1$ receptor antagonism (compounds 21, 22). These data are consistent with those reported by Drapeau et al.[15]. A second series of $B_1$ receptor antagonists, designed for labelling, was prepared following the report by Lévesque et al.[24] (see compounds 27, 28, 29 and 30 of Table 3). The four compounds maintain high affinity for the $B_1$ receptors of the RbA ($pA_2$ values of 8.10 to 8.5) and little, if any, residual agonistic activities on the $B_2$ receptors of the RbJV and the GPI. They are however broken down by ACE, especially those (compounds 27,28) which do not possess D-amino acid in position 7.

$B_1$ and $B_2$ receptor antagonists containing Oic in position 8 are presented in Table 4. These compounds, prepared by investigators at Hoechst and Scios were tested in the same assays as those of Tables 1, 2 and 3. All compounds exhibit complete resistance to ACE metabolism. All compounds are devoid of partial agonistic activity on both $B_1$ and $B_2$ receptor preparations. The presence of a D-residue in position 7 and of Oic in position 8 appear to be essential inasmuch for metabolic protection than for inactivity as agonists. All compounds presented in Table 4 are non selective and represent a new class of antagonists which are able to block both $B_1$ and $B_2$ receptors. The spectrum of biological activities shows some differences in that compounds 33 and 34 are more active on the $B_1$ receptor while compound 31 is more potent on the $B_2$ receptor (see Table 4). Worthy of mention is the interesting pharmacological characteristics of compounds 31, 32, 33 and 34 which are active on the bradykinin $B_2$ receptor of the RbJV as well as on the RbA while being almost inactive on the $B_2$ receptor of the GPI.

Activities of Some $B_1$ Receptor Antagonists on Human $B_1$ and $B_2$ Receptors.

Some peptidic compounds mentioned earlier were also tested on the HUV, a preparation that contains $B_1$ and $B_2$ receptors for the kinins[10]. The results summarized in Table 5, indicate that all compounds selected are pure $B_1$ receptor antagonists, showing no agonistic or antagonistic activities on the human $B_2$ functional site, with the exception of NPC 18828. The presence of a Lys at the N-terminal is important for the $B_1$ receptor antagonist since the affinity of Lys(Leu$^8$) desArg$^9$BK is higher than that of (Leu$^8$)desArg$^9$BK by at least 1.5 log units which is in agreement with the results of Menke et al.[25] who have cloned and characterized the human $B_1$ receptor. The presence of a D-Tic in position 7 is unfavourable for $B_1$ receptor antagonism, but the affinity of the antagonist can be markedly increased by the addition of a D-Arg at the N-terminal. Other substitutions in this position (with Sar, Ac Lys) are equally favourable in a series of compounds containing D-βNal in position 7. A significant gain of affinity for the $B_1$ receptor is observed when position 8 is occupied by Ile. Indeed, AcLys(D-βNal$^7$, Ile$^8$) desArg$^9$BK is the most active antagonist, showing a $pA_2$ of 8.49±0, 10, which is almost 1.5 log units higher than those of all precedent compounds. The stereospecificity of the residue βNal in position 7 is again crucial, likewise in the rabbit, since the isomeric form L-βNal shows 3 orders of magnitude less antagonistic activity than the D-βNal form. Two of the compounds designed for labelling through an elongation of the N-terminal show very high affinities for the human $B_1$ receptor and are inactive on the human $B_2$ receptor. These results are similar to what have been observed on the rabbit B, receptor. The Hoechst compound (S 0765) is a pure $B_1$ receptor antagonist ($pA_2$ 7.29) which is in contrast with its mixed $B_1$ and $B_2$ antagonistic activities on the rabbit tissues. The NPC 18828 behaves as an antagonist on both human $B_1$ and $B_2$ receptors with a marked predominance for the former. Worthy of notice is the overall resemblance in the pharmacological profiles of the human and the rabbit $B_1$ receptors described in the present study.

Discussion

The present analysis concerns four series of peptides designed to improve $B_1$ receptor antagonism and obtain compounds with high affinity, full selectivity for the $B_1$ receptor and resistance to degradation by ACE and possibly aminopeptidases. To these goals, substitutions were made in positions 3, 7 and 8 of (Leu$^8$)desArg$^9$BK and one residue or more were added to the N-terminal end, since Lys(Leu$^8$) desArg$^9$BK has been shown to be at least 10 times more active than (Leu$^8$)desArg$^9$BK in the rabbit[7,8] and the human[10,25].

Recent studies have shown that human kinins have a Hyp residue in position 3[26,27]. The reasons of this naturally-occurring hydroxylation of the proline at position 3 in the kinin analog sequences still awaits to be explained. It has been shown, by means of functional assays, that (Hyp$^3$) contained in bradykinin and its analogues may increase the affinity for the $B_2$ receptor of certain species such as rabbits[22,28] and dogs[22,28]. The majority of $B_2$ receptor antagonists of the first and second generation also contain a Hyp residue in position 3 (e.g. D-Arg(Hyp$^3$,D-Phe$^7$)BK[20], D-Arg(Hyp$^3$,D-Phe$^7$,Leu$^8$) BK[21]), and may be converted to desArg$^9$-derivatives (antagonists of the $B_1$ receptors) even in vitro by the intramural carboxypeptidases of some isolated organs[29]. The first series of compounds was therefore designed to evaluate the role of Hyp$^3$ and the results presented in Table 1 indicate that the Hyp in position 3 does not influence the antagonist affinities in the rabbit $B_1$ receptor.

Human and animal kallidins have a Lys residue at the N-terminal end, which may probably be the most abundant naturally-occurring kinin analogues present in human plasma and urine[30]. Furthermore, kallidin and desArg$^{10}$-kallidin are sensitive to aminopeptidases (e.g. Aminopeptidase M; EC 3.4.11.2) and can be protected by N-acetylation[15]. First and second generation of antagonists have however a D-Arg at the N-terminal, a substitution which has also been shown to protect against degradation by aminopeptidases (see Stewart and Vavrek)[31]. In the first three series (see Tables 1, 2 and 3), the role of the N-terminal position and the C-terminal portion, especially the positions 7 and 8, were conjointly investigated. Because of the predominant role played by ACE, the endothelial enzyme of the pulmonary circulation[32], in the inactivation of both the kinins and their desArg$^9$-metabolites, $B_1$ receptor antagonists must be protected if one wishes to prolong their in vivo activities. To this goal, D-Tic, a rigid phenylalanine surrogate which has been shown to be protective in HOE140[33] and D-βNal, a non-natural aromatic aminoacid, were used in the peptide sequence. Results summarized in Tables 2 and 3 clearly indicate that the presence of D-Tic in position 7 not only completely prevents the ACE from acting, but a D-residue is also essential for antagonism on the $B_1$ receptor (compare the two diastereoisomeric compounds 13 and 14 of Table 2). The major limitation of the D-Tic series is however their modest antagonistic affinity, which remains 1.5 log units below that of Lys(Leu$^8$)desArg$^9$BK. The fundamental role of a D-residue in position 7 for $B_1$ receptor antagonism is supported by the D-βNal series (Table 3) and especially by the comparison between compound 19 (which contains D-βNal) and compound 20 (which contains L-βNal). The presence of a D-βNal in position 7 not only protects (quite efficiently) from degradation by ACE, but confers higher affinity (by three log units) and selectivity for the rabbit and human $B_1$ receptors. The only limitation of compound 19 is its residual agonistic activity on the GPI, which appears to be due to a contractile effect of unknown nature, since it is not antagonized either by HOE140 (a β-2 receptor antagonist), or by Losartan (a $AT_1$ receptor antagonist), indomethacin (a cyclooxygenase inhibitor) and atropine (a muscarinic receptor antagonist) (data not shown). As for the Phe at position 8, several substitutions were made with Leu, Ile or Ala (in the second and third series) with the results of Ile being the most favourable residue for $B_1$ receptor antagonism. The presence of Ala in position 8 eliminates antagonistic activity, suggesting that a hydrophobic bulky residue is needed in position 8 for $B_1$ receptor antagonism. Lacking any knowledge of the geometrical topography of the $B_1$ receptor interacting sites, one can only speculate on the reasons of differential antagonistic potency observed between the (D-Tic$^7$)desArg$^9$BK analogs (second series) and the (D-βNal$^7$)desArg$^9$BK derivatives (third series). Indeed, the D-Tic residue because of its rigid and cyclic structure may exert a greater influence on peptide conformation than the D-βNal residue which has its side chain more flexible. Additionally, both residues because of their hydrophobic nature and their opposite stereochemical configuration may enable the accessibility on the receptor via a hydrophobic pouch.

Few peptidic compounds, d signed to obtain potential radioligands (to be labelled with $^{125}$I), were developed (see Table 3) following the recent report of Lévesque et al.[24] Two analogues (compounds 27, 28) based on Lys(Leu$^8$) desArg$^9$BK, the prototypic $B_1$ receptor antagonist, with an additionally extended N-terminal side, were developed. The results have demonstrated that they maintained high affinities on the human and rabbit $B_1$ receptors and they are subject to catabolism by ACE. The insertion at the C-terminal end of enzymatically protecting residues such as D-βNal in position 7 (compounds 29, 30) gave rise to more resistant and still selective $B_1$ receptor antagonists. The non radioactive iodinated peptide (compound 30) was synthesized in order to assess possible changes in affinity and enzymatic resistance of this latter peptide. No significant changes were seen on the pharmacological and biochemical properties of compound 29, thus the SarTyrϵFAhxLys(D-βNal$^7$, Ile$^8$)desArg$^9$BK (SEQ ID NO. 33) (compound 29) may have its usefulness in binding studies on the kinin $B_1$ receptors.

Use of Oic (a non-aromatic tryptophan-like derivative) in position 8 conjointly with a D-stereoorientation aminoacid in position 7, have been shown to possess important effects such as preservation of $B_2$ receptor antagonism, at least on the rabbit $B_2$ receptor subtype, and thus provides a new category of antagonists acting on both $B_1$ and $B_2$ receptors. These findings are consistent with previous studies[34,35] and can be extended with the results obtained with the antagonists NPC 18565 (compound 33; Scios) and NPC 18828 (compound 34; Scios). Considering the important role that is played by kinins in the acute (via the $B_2$ receptor) and chronic (via the $B_1$ receptor) phases of inflammation and pain[1,2], this type of compounds may become very useful to assess the role of kinins in experimental pathology. In fact, blockade of only one kinin receptor type, when both $B_1$ and $B_2$ receptors are involved will generally lead to partial protection and underestimation of antagonist affinities. The D-Arg(Hyp$^3$, Thi$^5$, D-Tic$^7$, Oic$^8$)desArg$^9$BK (S 0765) and the D-Arg(Hyp$^3$, D-Tic$^7$ (trans-thiophenyl), Oic$^8$) desArg$^9$BK (NPC 18828) have shown dissimilarity between human and rabbit $B_2$ receptor antagonism (see Tables 4 and 5). This may be explained by the existence of heterogeneous Bradykinin $B_2$ receptors between species and/or tissues.

Furthermore, this is supported by previous studies which have demonstrated that the S 0765 compound shows differential antagonistic potency between species[34,35]. In fact, the S 0765 compound is a poor $B_2$ receptor antagonist in humans (present study), rats[35] and guinea pigs[34,35] (present study) whereas it shows high potency in rabbit tissues[35] (present study). As shown in Table 5, NPC 18828 is a very active and quite selective antagonist of the human $B_1$ receptor, and interacts with the rabbit but not with the guinea pig $B_2$ receptor subtype (Table 4). The present structure-activity study has therefore provided indications on the stereochemical requirements that might contribute to high potency and selectivity for $B_1$ receptor antagonism. From the results presented above, it appears that the chemical features favouring affinity of antagonists on the human $B_1$ receptor are similar to those for the rabbit $B_1$ receptor, as already emphasized by Regoli et al.[36] and Gobeil et al.[10].

In summary, several peptides related to desArg$^9$-bradykinin were tested as stimulants or inhibitors of $B_1$ (rabbit aorta, human umbilical vein) and $B_2$ (rabbit jugular vein, guinea pig ileum, human umbilical vein) receptors. The compounds were also incubated with purified angiotensin converting enzyme from rabbit lung to test their resistance to degradation. Apparent affinities (in terms of $pA_2$) of compounds and their potential residual agonistic activities ($\alpha^E$) were evaluated. Bradykinin and desArg$^9$-bradykinin were used as agonists for the $B_2$ or the $B_1$ receptors, respectively. Degradation of peptides by the angiotensin-converting enzyme was prevented in the presence of a D-residue in position 7 of desArg$^9$-bradykinin. Replacement of Pro$^7$ with D-Tic combined with Leu, Ile, Ala or D-Tic in position 8 led to weak $B_1$ receptor antagonists, some of which with strong residual agonistic activities on the $B_2$ receptors preparations. Use of D-$\beta$Nal in position 7, combined with Ile in position 8 and Ac-Lys at the N-terminal (e.g. AcLys(D$\beta$-Nal$^7$, Ile$^8$) desArg$^9$BK) gave the most active $B_1$ receptor antagonist ($pA_2$ of 8.5 on the rabbit aorta and the human umbilical vein), which is also partially resistant to enzymatic degradation. Extension of the N-terminal end by Sar-Tyr-$\epsilon$Ahx (used for labelling purpose) and even cold labelling of Tyr with Iodine were compatible with high, selective and specific antagonism of the $B_1$ receptors. Some compounds were compared with those of some already known $B_1$ receptor antagonists to underline the novelty of new peptidic compounds.

EXAMPLE 2

B1-Bradykinin Receptor Blockade may Prevent Diabetes-Associated Vaculopathy

Capillary permeability is known to be selectively augmented in the streptozotocin (STZ) diabetic rat model[49]. The vascular BK receptors in the STZ-induced diabetic rat was examined. Segments of the portal vein (a known preparation for BK studies) from these rats were mounted in organ baths for isometric contraction studies. The response to desArg$^9$BK, a specific BK–$B_1$ receptor agonist, was enhanced by 118% in the diabetic tissue, compared to normal portal veins (0.48 vs 0.22g: P<0.001). This enhanced sensitivity was abolished by Lys(Leu$^8$)desArg$^9$BK, a specific antagonist of the BK–$B_1$ receptor. HOE140, the BK–B2 receptor antagonist, had no effect on the diabetic portal vein abnormality. Evans blue (EB: 20 mg/kg), a marker of albumin extravasation, was injected to unanesthetized diabetic rats. In two selected tissues where EB leakage was enhanced in diabetes (the skin and the pancreas (from 11 to 48, and from 44 to 92 ug/g dry tissue)), the BK–$B_1$ receptor antagonist normalized capillary permeability. HOE140 failed to correct EB extravasation in the two affected organs. Therefore, it was concluded that post-capillary hypercontractility to BK (via its $B_1$ receptor) forces EB extravasation, and likely contributed to the diabetic vasculopathy. From these results, it is contemplated that the $B_1$-antagonists described in Example 1, particularly those that are proteolysis-resistant, are now suitable for a drug-preventive approach to diabetic vasculopathy, by targeting $B_1$-receptor without being extensively degraded prior to reaching this receptor.

EXAMPLE 3

Hyperglycemia, Diuresis, Proteinuria, Nitrite and Kallikrein Urinary Excretion are all Normalized by $B_1$-BK Receptor Blockade:

Streptozotocin has been extensively used to produce type I diabetes in animals. This experimental disease is characterized by a mild inflammatory reaction in the Langerhans islets. Because kinins have been proposed as prominent inflammatory mediators in the pathogenesis of several diseases, we evaluated the role of kinins and their receptors in the evolution of insulitis. Male C57BL/Ks mdb mice were injected with streptozotocin (40 mg/kg) for 5 consecutive days. The kinin $B_1$ receptor antagonist (Leu$^8$)desArg$^9$BK or the $B_2$ antagonist HOE140 were injected subcutaneously to STZ mice at 300 ug/Kg bw twice a day and 500 ug/Kg per day, respectively. Treatment with antagonists was started 3 days after STZ and lasted for 10 days. Plasma glucose was determined by the glucose oxidase method, and 13 days urinary samples were assayed for proteins, nitrites and kallikreins. Diabetic mice showed hyperglycemia and increased diuresis, marked proteinuria and increased excretion of nitrites and kallikreins. The treatment with $B_2$ receptor antagonist did not show any effect on glycemia, but it reduced significantly water and protein excretion, compared to STZ group. STZ mice treated with $B_1$ receptor antagonist showed normal glycemia and complete normalization of diuresis, protein, nitrite and kallikrein excretion. The results obtained in the investigation support the assumption that the kallikrein kinin system intervenes in the maintenance of diabetic lesions and also indicates that $B_1$ kinin receptors play the most significant role in this experimental disease.

Repeated injections of streptozotocin over 5 days in the mouse have been shown to induce diabetes[44]. This experimental disease is characterized by a mild inflammatory reaction in the Langerhans islets (insulitis) and by changes of renal functions. Because of the important role that is played by kinins in various inflammatory states or tissue reactions[1], even in the pancreas[41] we raised the hypothesis that these peptides and their receptors could be implicated in the streptozotocin-induced diabetes. Recent findings indicate that $B_2$ receptors may play a role in the acute phases of inflammatory processes[42] while $B_1$ receptors are rather involved in the chronic phases of pain and inflammation[39]. The purpose of the present investigation was therefore to evaluate the possible role of kinins and their receptors in diabetic mice by the use of potent, selective and specific antagonists of the $B_2$ or the $B_1$ receptors.

Methods

Animals

Male C57BL/Ksmdb mice, 3 month old were provided by National Institute of Genetic, Buenos Aires. The animals were housed at a constant room temperature, with a 12 h light-dark cycle.

Animals were randomly divided into the following groups:
A: control treated with solvent.
B: treated with streptozotocin (STZ), 40 mg/kg, during 5 consecutive days
C: treated with STZ+$B_1$ antagonist: 3 days after the beginning of the treatment with STZ, the animals were injected twice a day with the $B_1$ receptor antagonist (Leu$^8$) desArg$^9$BK (300 ug/kg) subcutaneously for 10 days
D: treated with STZ+$B_2$ antagonist: 3 day after treatment with STZ, the animals received D-Arg(Hyp$^3$Thi$^5$, D Tic$^7$, Oic$^8$)BK (HOE140) 500 ug/Kg/day subcutaneously during 10 days.
E and F groups received only (Leu$^8$)desArg$^9$BK and HOE140 respectively.

Biochemical Assays

Blood (50–60 ul) was collected from the tail vein of non fasting animals in heparinized capillary tubes. Blood samples were taken one day before starting the STZ injection and at the day 13, just before sacrifice. Blood samples were centrifuged and the plasma immediately diluted into the appropriate buffer. Plasma glucose was determined by a glucose oxidase method (the kit was obtained from Wiener, Argentina). Urinary samples were collected over 24 h in housed metabolic cages on the day 13. Urinary volume was determined gravimetrically and urinary samples were assayed for proteins[45], nitrites[40] and kallikrein[47].

Chemicals

Streptozotocin was purchased from the Sigma Chem Co., St. Louis, Mo. It was dissolved in 0.02 M citrate buffer pH, 4.5 and immediately injected intraperitoneally. (Leu$^8$) desArg$^9$BK was purchased from Sigma Chem Co., and HOE140 was kindly provided by Dr. B. Schölk ns from HOECHST, Frankfurt, Germany. Kallikrein assay was performed using synthetic chromogenic substrate H-D-Val-Leu-Arg-pNA (S-2266) from Kabi, Stockholm, Sweden. The paranitroanilide (pNA) released by enzymatic action on the substrate was measured calorimetrically to determine kallikrein activity Statistical Analysis All data were expressed as mean=S.E. Analysis of Variance (ANOVA) was performed to evaluate differences among the groups. $p<0.05$ was considered as significant.

Results

Effects of the $B_2$ Receptor Antagonist, HOE140

The results obtained in the groups of animals used to evaluate the role of $B_2$ receptors are presented in FIG. 1. The effect of HOE140 in control and diabetic mice was evaluated by measuring body weight, glycemia and renal functions, particularly urinary volume, proteinuria, kallikrein and nitrites urinary excretion. No changes of body weight were observed between the various groups of mice.

The two groups treated with STZ showed a significant increase of blood glucose: the treatment with $B_2$ receptor antagonist did not show any effect on glycemia.

Diabetic mice (STZ) showed increased diuresis, marked proteinuria, as well as increased excretion of nitrites and kallikreins. When treated with HOE140, the diabetic animals showed significant reduction in the renal functions, compared to the STZ group. Urinary volume was however reduced only by half and still remained significantly elevated with respect to controls; the same was found to be true for protein and nitrite excretion. Kallikrein excretion was brought back to normal by the treatment with HOE140.

Effects of the $B_1$ Receptor Antagonist, (Leu$^8$)desArg$^9$BK.

Results obtained in the group of mice used to evaluate the effects of $B_1$ receptor antagonist are summarized in FIG. 2. Body weight was similar in all groups STZ treated mice showed significant increase of glycemia, urinary volume, as well as protein, nitrite and kallikrein excretion, similar to those of the group analysed in FIG. 1. STZ mice treated with the $B_1$ receptor antagonist, showed normal glycemia, thus indicating that blockage of $B_1$ receptors is associated with a normalization of the blood glucose. Treatment with the $B_1$ antagonist was effective also in preventing the increase of the urinary volume, as well as those of protein, nitrite and kallikrein in the urine, that is normally observed in diabetic mice.

Discussion

Streptozotocin-induced diabetes in the mouse is associated with an inflammatory reaction[38] of the Langerhans islets[46] with incremented production of NO[37] and with modifications of renal functions. We hypothesized that the kallikrein-kinin system may intervene in the pathogenesis of this experimental disease, both at the pancreas and at the renal levels. The results obtained in the present investigation support entirely our assumption and also indicate that the kinin receptor that plays the most significant role may be the $B_1$. This conclusion is based on the observation that prolonged (10 days) treatment with (Leu$^8$)desArg$^9$BK is associated with a correction of the biochemical parameters that characterize STZ-induced diabetes. Blood glucose of STZ+$B_1$ antagonist group was normal, indicating that $B_1$ receptors play a determinant role in the inflammatory reaction of the Langerhans islets and that this reaction is responsible for the elevation of the blood glucose. When the islet inflammation (insulitis) is prevented, glycemia will remain within normal values. At the kidney level, the two most important changes are the increase of urinary volume and protein excretion, which depend on an augmented permeability of the glomerular membrane. The present results support the interpretation that STZ-induced diabetes is associated with the appearance of $B_1$ receptor in the glomerular membrane and that stimulation of this receptor leads to diuresis and proteinuria. Indeed appearance of $B_1$ receptors has been demonstrated in STZ diabetic rats. If $B_1$ receptors are blocked the two renal parameters are brought back to normal. How can these receptors be activated? Probably by kinins and their metabolites whose production in the pancreas may be increased during insulitis. If insulitis is prevented, glycemia remains normal, the kallikrein-kinin system is not activated and the renal function are not modified. The determinant role of $B_1$ receptors is confirmed by the comparison with the $B_2$ antagonist treated group.

Block of $B_2$ receptors does not lead to correction of glycemia, supporting the interpretation that insulitis is a slowly developing inflammatory reaction, primarily mediated by $B_1$ receptors. $B_2$ receptors may play a role at the kidney level, in the glomerular membrane, where their activation may lead to increase of permeability. This mechanism is invoked to explain the partial correction of diuresis, proteinuria and the total correction of kallikrein which was found in the HOE140 treated mice. Together with the changes of the kallikrein-kinin excretion, which increases, in accord with Harvey et al, 1990, and with the induction of the $B_1$ receptor, NO excretion in urines was also found to be increased: this probably reflects increased production of NO from inflammatory (the Langerhans islets) sites as already reported by Catanzaro et al, 1994. In conclusion, STZ treatment leads to insulitis, which is probably associated with the activation of the kallikrein-kinin system and with the de novo formation of $B_1$ receptors, which appear to play the major role in the inflammatory reaction and in hyperglycemia. Kinins produced at the pancreas level may reach the kidney and activate $B_2$ and $B_1$ receptors in the glomerular membrane; such activation results in an increase of permeability which is responsible for diuresis and proteinuria.

EXAMPLE 4

Enhanced Response of the $B_1$-Bradykinin Receptor in the Spontaneously Hypertensive Rat We have previously examined the contractile response of the portal vein (a suitable preparation for $B_1$-BK studies) obtained from untreated 8-week old spontaneously hypertensive rats (SHR)[48], in order to document an eventual exaggerated contraction of this post-capillary vascular preparation, susceptible to enhance capillary hydrostatic pressure and plasma leakage described in the SHR[50].

Desendothelialized portal vein segments obtained from SHR were mounted in organ baths containing a Krebs solution supplemented with captopril (3 uM), for isometric contraction studies (baseline tension: 0.5 g). The selective $B_1$-BK agonist, des-$Arg^9$_BK was administered on portal vein segments obtained from normal rats and SHR, to establish dose-response curves to DesArg$^9$BK, from $10^{-9}$ to $10^{-5}$ M.

For all values higher than $10^{-8}$M, the contraction curves obtained with portal vein samples from SHR were 72% to 100% higher than those observed in control rats. However, the apparent affinity of the agonist for its receptor, defined as the $EC_{50}$ remained unchanged. Addition to the bath of a specific $B_1$-BK receptor antagonist, Lys(Leu$^8$)-des-Arg$^9$-BK (2 ug/ml), completely blocked the portal vein contraction induced by the $B_1$-BK receptor agonist in the control rats and in the SHR.

These results revealed for the first time, an abnormality of the $B_1$-BK receptor on the venous side of the splanchnic microcirculation in the untreated SHR. This defect was characterized by an enhanced sensitivity of the $B_1$-BK receptor, which likely resulted in a twofold increment in the splanchnic post-capillary resistance. As a result, hydrostatic pressure rises in this, and presumably, other microcirculation beds. Enhanced plasma extravasation from the vascular to the interstitial compartment previously described in the SHR, could well be related to this unique abnormality of the $B_1$-BK receptor.

In view of the above results (Examples 2 to 4), it is contemplated that the preferred $B_1$-antagonists described in Example 1 can be advantageously used in replacement of Lys(Leu$^8$)desArgBK. Particularly, compounds 8,9,12,13,17 to 19, and 23 to 30, which appear to be at least 2 to 5 times less susceptible to ACE proteolytic degradation, may be dosed to achieve an effect equivalent to the one observed in vivo in STZ-mic with a dosage regimen of 300 µg/Kg b.i.d. subcutaneously (see Example 3). The doses of the novel $B_1$-antagonists need to be adjusted to take into account the pharmacokinetic and pharmacodynamic principles well known in the art: mode of administration, absorption, distribution, clearance, effective dose, side effects, etc. The antagonists of the present invention are the first to be usable for conducting more extensive clinical studies, since they combine acceptable affinity, selectivity and, in some instances, resistance to degradation.

This invention has been described hereinabove, and it is apparent that modifications can be made thereto, without departing from the teachings and the spirit of the invention. These modifications are under the scope of this invention, as defined in the appended claims.

TABLE 1

Pharmacological characterization and metabolic degradation (by ACE) of synthetic peptides

| | Abbreviated structure | SEQ ID NO | Rb.A. pA$_2$ | Rb.A. α$^E$ | Rb.J.V. pA$_2$ | Rb.J.V. α$^E$ | G.P.I. pA$_2$ | G.P.I. α$^E$ | ACE (% degradation) |
|---|---|---|---|---|---|---|---|---|---|
| 1 | (Leu$^8$)desArg$^9$BK | | 7.24 ± 0.10 | 0 | Inactive | 0 | Inactive | 0.07 | 83 ± 2 |
| 2 | Lys(Leu$^8$)desArg$^9$BK | | 8.45 ± 0.12 | 0 | Inactive | 0 | Inactive | 0 | 74 ± 2 |
| 3 | Lys(Hyp$^3$, Leu$^8$)desArg$^9$BK | | 8.16 ± 0.05 | 0.02 | Inactive | 0.02 | Inactive | 0 | 40 ± 3 |
| 4 | D-Arg(Hyp$^3$, Leu$^8$)desArg$^9$BK | | 6.47 ± 0.15 | 0 | Inactive | 0 | <5.02 | 0.38 | 83 ± 2 |
| 5 | AcLys(Hyp$^3$, Leu$^8$)desArg$^9$BK | | 6.75 ± 0.21 | 0 | Inactive | 0.03 | <5.02 | 0.30 | 66 ± 1 |
| 6 | D-Arg(Hyp$^3$, D-Phe$^7$)desArg$^9$BK | | 6.44 ± 0.05 | 0 | 5.63 ± 0.05 | 0 | <5.05 | 0.15 | n.d. |
| 7 | D-Arg(Hyp$^3$, D-Phe$^7$, Leu$^8$)desArg$^9$BK | | 6.56 ± 0.15 | 0 | 5.68 ± 0.04 | 0 | Inactive | 0 | n.d |

Data of bioassays are means s.e.m. of 4–7 experiments. Data from biochemical assays are means s.e.m. of 2–3 experiments.
Abbreviations: Rb.A. (rabbit aorta); Rb.J.V. (rabbit jugular vein); G.P.I. (guinea pig ileum); n.d. (not determined).
pA$_2$: -Log$_{10}$ of the molar concentration of the antagonist required to reduce the effect of a double concentration of agonist to a single one.
Degradation by ACE was evaluated after 30 min of incubation of peptide (200 µmol/L) with ACE (9 µg) (see Methods). Inactive mans that the compound shows no detectable antagonistic effect at concentration $\leq$ 10 µg/ml.

TABLE 2

Pharmacological characterization and metabolic degradation (by ACE) of synthetic peptides

| | Abbreviated Structure | SEQ ID NO. | Rb.A. pA$_2$ | Rb.A. α$^E$ | Rb.J.V. pA$_2$ | Rb.J.V. α$^E$ | G.P.I. pA$_2$ | G.P.I. α$^E$ | ACE (% degradation) |
|---|---|---|---|---|---|---|---|---|---|
| 8 | (D-Tic$^7$, Leu$^8$)desArg$^9$BK | 12 | 5.86 ± 0.03 | 0 | Inactive | 0.10 | Inactive | 0.18 | 0 |
| 9 | Sar(D-Tic$^7$, Leu$^8$)desArg$^9$BK | 13 | 6.16 ± 0.01 | 0 | Inactive | 0 | Inactive | 0.07 | 0 |
| 10 | Lys(D-Tic$^7$, Leu$^8$)desArg$^9$BK | 14 | 6.50 ± 0.02 | 0 | <5.20 | 0.44 | F.ag. | 1.01 | n.d. |
| 11 | AcLys(D-Tic$^7$, Leu$^8$)desArg$^9$BK | 15 | 5.17 ± 0.04 | 0 | Inactive | 0.37 | *5.85 ± 0.11 | 1.02 | 0 |
| 12 | D-Arg(D-Tic$^7$, Leu$^8$)desArg$^9$BK | 16 | 6.70 ± 0.06 | 0 | 5.35 ± 0.12 | 0 | Inactive | 0.02 | 0 |
| 13 | D-Arg(D-Tic$^7$, Ile$^8$)desArg$^9$BK | 17 | 6.97 ± 0.04 | 0 | 5.34 ± 0.01 | 0 | Inactive | 0.02 | 9 ± 1 |
| 14 | D-Arg(L-Tic$^7$, Ile$^8$)desArg$^9$BK | 18 | <5.04 | 0 | 5.19 ± 0.06 | 0 | Inactive | 0 | 77 ± 3 |

TABLE 2-continued

Pharmacological characterization and metabolic degradation (by ACE) of synthetic peptides

| | Abbreviated Structure | SEQ ID NO. | Rb.A. pA$_2$ | α$^E$ | Rb.J.V. pA$_2$ | α$^E$ | G.P.I. pA$_2$ | α$^E$ | ACE (% degradation) |
|---|---|---|---|---|---|---|---|---|---|
| 15 | D-Arg(D-Tic$^7$, Ala$^8$)desArg$^9$BK | 19 | <5.02 | 0 | Inactive | 0 | P.ag. | 0.47 | 21 ± 1 |
| 16 | D-Arg(Hyp$^3$, D-Tic$^7$)desArg$^9$BK | 20 | 6.73 ± 0.02 | 0 | <5.66 | 0.51 | P.ag. | 0.63 | 0 |
| 17 | D-Arg(Hyp$^3$, D-Tic$^7$, Leu$^8$)desArg$^9$BK | 21 | 6.64 ± 0.01 | 0 | <5.04 | 0 | Inactive | 0.09 | 0 |

Abbreviation as in TABLE 1
*pD$_2$ indicating apparent affinity as an agonist. n.d.: not determined; F.ag.: full agonist; P.ag.: partial agonist.

TABLE 3

Pharmacological characterization and metabolic degradation (by ACE) of synthetic peptides

| | Abbreviated structure | SEQ ID NO. | Rb.A. pA$_2$ | α$^E$ | Rb.J.V. pA$_2$ | α$^E$ | G.P.I. pA$_2$ | α$^E$ | ACE (% degradation) |
|---|---|---|---|---|---|---|---|---|---|
| 18 | AcLys(D-βNal$^7$, Leu$^8$)desArg$^9$BK | 22 | 7.91 ± 0.08 | 0 | <5.06 | 0 | Inactive | 0 | 22 ± 1 |
| 19 | AcLys(D-βNal$^7$, Ile$^8$)desArg$^9$BK | 23 | 8.40 ± 0.12 | 0 | Inactive | 0.09 | P.ag. | 0.38 | 34 ± 1 |
| 20 | AcLys(L-βNal$^7$, Ile$^8$)desArg$^9$BK | 24 | 5.30 ± 0.03 | 0 | 5.11 ± 0.05 | 0 | Inactive | 0.06 | 99 ± 1 |
| 21 | $^a$AcLys(N-MeAla$^6$, Leu$^8$)desArg$^9$BK | 25 | 6.55 ± 0.06 | 0.01 | Inactive | 0 | Inactive | 0.19 | 0 |
| 22 | AcLys(N-MeAla$^6$, D-βNal$^7$, Ile$^8$)desArg$^9$BK | 26 | 6.27 ± 0.06 | 0 | Inactive | 0.03 | P.ag. | 0.52 | 0 |
| 23 | D-Arg(D-βNal$^7$, Ile$^8$)desArg$^9$BK | 27 | 7.72 ± 0.11 | 0.02 | 6.37 ± 0.12 | 0.10 | P.ag. | 0.48 | 8 ± 1 |
| 24 | D-Arg(D-βNal$^7$, Leu$^8$)desArg$^9$BK | 28 | 7.30 ± 0.03 | 0 | 5.44 ± 0.09 | 0 | Inactive | 0 | 5 ± 1 |
| 25 | D-Lys(D-βNal$^7$, Ile$^8$)desArg$^9$BK | 29 | 7.71 ± 0.05 | 0 | 5.43 ± 0.11 | 0.02 | P.ag. | 0.33 | 9 ± 2 |
| 26 | Sar(D-βNal$^7$, Ile$^8$)desArg$^9$BK | 30 | 7.42 ± 0.06 | 0 | 5.04 ± 0.01 | 0.11 | P.ag. | 0.68 | 0 |
| 27 | AcTyrεAhxLys(Leu$^8$)desArg$^9$BK | 31 | 8.10 ± 0.08 | 0 | Inactive | 0.03 | P.ag. | 0.30 | 52 ± 1 |
| 28 | SarTyrεAhxLys(Leu$^8$)desArg$^9$BK | 32 | 8.17 ± 0.06 | 0 | Inactive | 0 | Inactive | 0.19 | 34 ± 3 |
| 29 | SarTyrεAhxLys(D-βNal$^7$, Ile$^8$)desArg$^9$BK | 33 | 8.48 ± 0.03 | 0 | 5.20 ± 0.13 | 0.02 | Inactive | 0 | 15 ± 1 |
| 30 | SarTyr(3,5-I)εAhxLys(D-βNal$^7$, Ile$^8$)desArg$^9$BK | 34 | 8.14 ± 0.05 | 0 | 5.13 ± 0.05 | 0 | Inactive | 0 | 13 ± 1 |

Abbreviations as in TABLE 1
$^a$from ref. Drapeau et al., 1994. P.ag.: partial agonist

TABLE 4

Pharmacological characterization and metabolic degradation (by ACE) of synthetic peptides

| | Abbreviated structure | SEQ ID NO. | Rb.A. pA$_2$ | α$^E$ | Rb.J.V. pA$_2$ | α$^E$ | G.P.I. pA$_2$ | α$^E$ | ACE (% degradation) |
|---|---|---|---|---|---|---|---|---|---|
| 31 | $^a$D-Arg(Hyp$^3$, Thi$^5$, D-Tic$^7$, Oic$^8$)desArg$^9$BK (S 0765) | 35 | 6.80 ± 0.10 | 0 | 7.38 ± 0.02 | 0 | <5.12 | 0 | 0 |
| 32 | $^a$(Hyp$^3$, Thi$^5$, D-Tic$^7$, Oic$^8$)desArg$^9$BK (S 1629) | 36 | 6.32 ± 0.02 | 0 | 6.35 ± 0.02 | 0 | <5.12 | 0 | 0 |
| 33 | D-Arg(Hyp$^3$, D-Hyp$^7$(trans propyl), Oic$^8$)desArg$^9$BK (NPC 18565) | 37 | 7.94 ± 0.06 | 0 | 6.99 ± 0.04 | 0 | <5.12 | 0 | 0 |
| 34 | D-Arg(Hyp$^3$, D-Hyp$^7$(trans thiophenyl), Oic$^8$)desArg$^9$BK (NPC 18828) | 38 | 8.27 ± 0.14 | 0 | 7.52 ± 0.05 | 0 | <5.14 | 0 | 0 |

Abbreviations as in TABLE 1
$^a$from ref. Wirth et al., 1991.

TABLE 5

Biological activities of desArg$^9$BK related peptides on the human B$_1$ and B$_2$ receptors of the umbilical vein

| | Human umbilical vein | | |
|---|---|---|---|
| | B$_1$ receptor | | B$_2$ receptor |
| Abbreviated structure | pA$_2$ | α$^E$ | pA$_2$ |
| (Leu$^8$)desArg$^9$BK | $^a$6.37 ± 0.06 | 0 | $^a$Inactive |
| Lys(Leu$^8$)desArg$^9$BK | $^a$7.99 ± 0.01 | 0 | $^a$Inactive |
| (D-Tic$^7$, Leu$^8$)desArg$^9$BK | 5.56 ± 0.04 | 0 | Inactive |
| D-Arg(D-Tic$^7$, Ile$^8$)desArg$^9$BK | 7.64 ± 0.12 | 0 | Inactive |
| D-Arg(L-Tic$^7$, Ile$^8$)desArg$^9$BK | 5.33 ± 0.17 | 0 | Inactive |
| D-Arg(D-βNal$^7$, Leu$^8$)desArg$^9$BK | 7.30 ± 0.07 | 0 | Inactive |
| Sar(D-βNal$^7$, Ile$^8$)desArg$^9$BK | 7.32 ± 0.01 | 0 | Inactive |
| Ac-Lys(D-βNal$^7$, Leu$^8$)desArg$^9$BK | 7.45 ± 0.04 | 0 | Inactive |

TABLE 5-continued

Biological activities of desArg⁹BK related peptides on the human $B_1$ and $B_2$ receptors of the umbilical vein

| | Human umbilical vein | | |
|---|---|---|---|
| | $B_1$ receptor | $B_2$ receptor | |
| Abbreviated structure | $pA_2$ | $\alpha^E$ | $pA_2$ |
| Ac-Lys(D-βNaI⁷, Ile⁸)desArg⁹BK | 8.49 ± 0.10 | 0 | Inactive |
| Ac-Lys(L-βNaI⁷, Ile⁸)desArg⁹BK | 5.16 ± 0.05 | 0 | Inactive |
| SarTyrϵAhxLys(D-βNaI⁷, Ile⁸)desArg⁹BK | 8.39 ± 0.16 | 0 | Inactive |
| SarTyr(3,5-I)ϵAhxLys(D-βNaI⁷, Ile⁸)desArg⁹BK | 8.32 ± 0.20 | 0 | Inactive |
| D-Arg(Hyp³, Thi⁵, D-Tic⁷, Oic⁸)desArg⁹BK | 7.29 ± 0.07 | 0 | Inactive |
| D-Arg(Hyp³, D-Hyp⁷ (trans thiophenyl), | 8.55 ± 0.09 | 0 | 5.12 ± 0.20 |

Abbreviations as in TABLE 1.
ᵃdata from Gobeil et al. 1996. n = 4–7 experiments.
Other suitable desArg⁹BK related peptides include: Sar(D-Tic⁷, Ile⁸)desArg⁹ Bradykinin (SEQ ID NO. 39), AcLys(D-Tic⁷, Ile⁸)desArg⁹ Bradykinin (SEQ ID NO. 40), D-Lys(D-βNaI⁷, Leu⁸)desArg⁹ Bradykinin (SEQ ID NO. 41), Sar(D-βNaI⁷, Leu⁸)desArg⁹ Bradykinin (SEQ ID NO. 42), AcTyrϵAhxLys(Ile⁸)desArg⁹ Bradykinin (SEQ ID NO. 43), SarTyrϵAhxLys(Ile⁸)desArg⁹ Bradykinin (SEQ ID NO. 44), SarTyrϵAxLys(D-NaI⁷, Leu⁸)desArg⁹ Bradykinin (SEQ ID NO. 45), SarTyr(3,5-iodine)AhxLys(D-NaI⁷ Leu⁸)desArg⁹ Bradykinin (SEQ ID NO. 46).

REFERENCES

1. Dray A, Perkins M. Bradykinin and inflammatory pain. Trends in Neurosci. 1993; 16:99–104.
2. Davis A J, Kelly D, Perkins M N. The induction of des-Arg⁹-bradykinin-mediated hyperalgesia in the rat by inflammatory stimuli. Brazilian J. Med. Biol. Res. 1994; 27:1793–1802.
3. Alvarez A L., Delorenzy A, Santajuliana D, Finkielman S, Nahmod V E, Pirola C J. Central bradykininergic system in normotensive and hypertensive rats. Clin. Science 1992;82:513–519.
4. Chakir M, Regoli D, Sirois P, Gobeil F, Plante G E Hypersensibilitéddu récepteur $B_1$ de la bradykinine au niveau de la veine porte de rat diabetique. Medecine/Sciences/1995; 11 (suppl.2): 15.
5. Zuccollo A, Navarro M, Catanzaro O. Effects of $B_1$ and $B_2$ kinin receptor antagonists in diabetic mice. Can. J. Physiol. Pharmacol. 1996; 74:586–589. Marceau F. Kinin $B_1$ receptors: a review. Immunopharmacol. 1995;30:1–26.
7. Regoli D, BarabéJ, Park WK. Receptors for bradykinin in rabbit aortae. Can. J. Physiol. Pharmacol. 1977; 55:855–867.
8. Regoli D, BarabéJ. Pharmacology of bradykinin and related kinins. Can. J. Physiol. Pharmacol. 1980; 32:1–46.
9. Erdös K G, Skidgel R A. The unusual substrate specificity and the distribution of human angiotensin I converting enzyme. Hypertension 1986; 8:34–37.
10. Gobeil F, Pheng L H, Badini I, Nguyen-Le X K, Pizard A, Rizzi A, Blouin D, Regoli D. Receptors for kinins in human isolated umbilical vein. Brit. J. Pharmacol. 1996; 118:289–294.
11. Gaudreau P, BarabéJ, St-Pierre S, Regoli D. Pharmacological studies of kinins on venous smooth muscles. Can. J. Physiol. Pharmacol. 1981; 59:371–379.
12. Furchgott R F, Bhadrakom S. Reaction of strips of rabbit aorta to epinephrine isopropyl arterenol and other drugs. J. Pharmacol. Exp. Ther. 1953; 108:124–143.
13. Rang H P. Stimulant actions of volatile anaesthetics on smooth muscle. Brit. J. Pharmacol. 1964; 22:356–365.
14. Schild H O. pA, a new scale for the measurement of drug antagonism. Brit. J. Pharmacol. 1947; 2:189–206.
15. Drapeau G, Audet R, Lévesque L, Godin D, Marceau F. Development and in vivo evaluation of metabolically resistant antagonists of $B_1$ receptors for kinins. J. Pharmacol. Exp. Ther. 1993; 266:192–198.
16. Gobeil F, Filteau C, Pheng L H, Jukic D, Nguyen-Le X K, Regoli D. In vitro and in vivo characterization of $B_2$ receptors in the rabbit and the guinea pig. Can. J. Physiol. Pharmacol. 1996; 74:137–144.
17. Wirth K, Breipohl G, Stechl J, Knolle J, Henke S, Schölkens B A. DesArg⁹-D-Arg(Hyp³,Thi⁵D-Tic⁷,Oic⁸) bradykinin (desArg¹⁰-(HOE140)) is a potent bradykinin $B_1$ receptor antagonist. Eur. J. Pharmacol. 1991; 205: 217–218.
18. Drapeau G, Regoli D. Synthesis of bradykinin analogues. Methods Enzymol. 1988; 163:263–272.
19. IUPAC-IUB Joint Commission on Biochemical Nomenclature (JCBN). Nomenclature and symbolism for amino acids and peptides. Eur. J. Biochem. 1983; 138:9–37.
20. Vavrek, R J and Stewart, J M. New bradykinin antagonists peptides as tools for the study of the kallikrein-kinin system. (n: Renal Function, Hypertension and Kallikrein-kinin System. pp 85–89. O. limura and H S Margolius, Eds. Univ. of Tokyo Press, Tokyo, 1988.
21. Regoli D, Rhaleb Nebr., Dion S, Drapeau G. New selective bradykinin receptor antagonists and bradykinin $B_2$ receptor characterization. Trends in Pharmacol. Sci. 1990; 11: 156–161.
22. Rhaleb N E., Télémaque S, Rouissi N, Dion S, Jukic D, Drapeau G, Regoli D. Structure activity studies of bradykinin and related peptides; $B_2$-receptor antagonists. Hypertension 1991; 17: 107–115.
23. Togo, J., Burdi, R M, De Haas, C J, Connor, J R and Steranka, L R. D-Phe⁷-substituted peptide bradykinin antagonists on not substrates for kininase II. Peptides 10:109–112, 1989.
24. Lévesque L, Harvey N, Rioux F, Drapeau G, Marceau F. Development of a binding assay for the $B_1$ receptors for kinins. Immunopharmacol. 1995; 29:141–147.
25. Menke J G, Borkowski J A, Bierilo K. K., MacNeil T, Derrick A W, Schneck K A., Ransom R W, Strader C D, Linemeyer D L, Hess J F. Expression cloning of a human $B_1$ bradykinin receptor J. Biol. Chem. 1994; 269:21583–21586.
26. Maier M, Ressert G, Jerabek I, Lottspeich F, Binder B R. Identification of (hydroxyproline³)-lysyl-bradykinin released from human kininogens by human urinary kallikrein. FEBS Lett. 1988; 232:395–398.
27. Kato H, Matsumuara Y, Maeda H. Isolation and identification of hydroxyproline analogues of bradykinin in human urine. FEBS Lett. 1988; 232:252–254.
28. Rhaleb N E., Drapeau G, Dion S, Jukic D, Rouissi N E., Regoli D. Structure-activity studies on bradykinin and related peptides: agonists. Brit. J. Pharmacol. 1990; 99:445–448.
29. Regoli D, Drapeau G, Rovero P, Dion S, Rhaleb N E., Barabé J, D'Orléans-Juste P, Ward P. Conversion of kinins and their antagonists into $B_1$ receptor activators and blockers in isolated vessels. Eur. J. Pharmacol. 1986; 127:219–224.

30. Hilgenfeldt U, Linke R, Riester U, König W, Breipohl G. Strategy of measuring bradykinin and kallidin and their concentration in plasma and urine. Analyt. Biochem. 1995; 228:35–41.
31. Stewart, J M and Vavrek, R J. Chemistry of peptide $B_2$ bradykinin antagonists. In: Bradykinin Antagonists: Basic and Clinical Research. R. M. Burch Ed. Marcel Dikker, N.Y., 1991.
32. Ferreira S H, Vane J R. The disappearance of bradykinin and eledoisin in the circulation and vascular beds of the cats. Br. J. Pharmacol. 1967; 108:124–143.
33. Hock F J, Wirth K, Albus U, Linz W, Gerhards H J, Wiemer G, Henke S, Breipohl G, Konig W, Knolle J, Scholkens B A. HOE 140, a new potent and long-acting bradykinin antagonist: in vitro studies. Brit. J. Pharmacol. 1991; 102:769–773.
34. Rhaleb N E., Gobeil F, Regoli D. Non-selectivity of new bradykinin antagonists for $B_1$ receptor. Life Sci. 1992; 51:125–129.
35. Regoli D, Gobeil F, Nguyen Q T, Jukic D, Seoane P R, Salvino J M, Sawutz D G. Bradykinin receptor types and $B_2$ subtypes. Life Sci. 1994; 55:735–749.
36. Regoli D, Pheng L H, Nsa Allogho S, Nguyen-Le X K, Gobeil F. Receptors for kinins: from classical pharmacology to molecular biology. Immunopharmacol. 1996 (in press).
37. Catanzaro, O L., Marina Prendes, M. G., Hope, S., Zuccollo, A., Dominguez, A. 1994. Streptozotocin-induced hyperglycemia is decreased by nitric oxide inhibition. Brazilian J. Med. Biol. Res; 27:2043–2047.
38. Cooke, A. 1990. AN overview on possible mechanisms of destruction of the insulin-producing B cells. Curr. Top. Microbiol. Immunol.; 164: 125–142.
39. Davis, A. J., and Perkins, M. 1994. The involvement of bradykinin B1 and B2 receptor mechanisms in cytokin-induced mechanical hyperalgesia in the rat. Br. J. Pharmocol.; 113:63–68.
40. Green, L. C, Wagner, D. A., Glogowski, J., Skipper, P. L., Wishnokj, S., Tennenbaum, S. R. 1982 Analysis of nitrate, nitrite and ($^{15}$N) nitrite in biological fluids. Anal. Biochem.; 126: 131–138.
41. Griesbacher, R. and Lembeck, F. 1992. Effects of the bradykinin antagonist, HOE140, in experimental acute pancreatitis. Br. J. Pharmacol.; 107: 356–360.
42. Hall J. M. 1992. Bradykinin receptors. Pharmacological properties and biological roles. Pharm. Ther.; 56: 131–190.
43. Harvey, J. N., Edmundson, A. W., Mayfield, R K 1990. Renal kallikrein in IDDM patients with glomerular hyperfiltration. Diabetes; 39:72A.
44. Kolb-Bachofen, V., Epstein, S., Kiesel, J., Kolb, H. 1988. Low dose streptozotocin-induced diabetes In mice. Electron microscopy reveals single cell insulitis before diabetes onset. Diabetes; 37:2 1–27.
45. Lowry, O. H., Rosenbrough, N. J., Farr, A. L., Randall, R. J. 1951. Protein measurement with Folin phenol reagent. J. Biol. Chem.; 193:265–275.
46. Mandrup-Poulsen, T., Bendtzen, K., Nielsen, J. H., Bendixen, G., Nerup, J. 1985 Cytokines cause functional and structure damage to isolate islets of Langerhans. Allergy; 40:424–490.
47. Vila, S. B., Peluffo, V., Alvarado, C., Cresto, J. C., Zuccollo, A., Catanzaro, O. L. 1992. The kallikrein kinin system in early state of diabetes. In Agents and Actions. Recent Progress on Kinins. Edited by Bonner et al. Birkhauser-Basel 38 (III) pp 304–310.
48. Chakir, M., Regoli, D., Sirois, P., Gobeil, R., Plante, G. E. 1996. Hypersensibilité du récepteur $B_1$ de la bradykinine au niveau de la veine porte de rat spontanément hypertendu (SHR) 1996 Medecine/Sciences; 12(suppl. 1): 12.
49. (1995). Eur. J. Pharmacol.; 285: 11.
50. (1992) J. Clin. Invest.; 89: 2030.

We claim:

1. A method of treating a $B_1$-bradykinin receptor mediated inflammatory condition in a mammal, said method comprising the step of administering to said mammal a therapeutically effective amount of a $B_1$-bradykinin receptor antagonist of the Formula I:

A-Arg-Pro-B-Gly-Phe-Ser-C-E (Formula I, SEQ ID NO: 47 or SEQ ID NO: 48), wherein the groups A, B, C and E are independently defined and with the proviso that said $B_1$-bradykinin receptor antagonist is not SEQ ID NO: 15 or SEQ ID NO: 16, wherein said $B_1$-bradykinin receptor antagonist is administered under conditions effective to ameliorate the $B_1$-bradykinin receptor mediated inflammatory condition in said mammal.

2. The method of claim 1, wherein said condition is selected from the group consisting of a diabetic vasculopathy, diabetic symptoms associated with an insulitis and a post-capillary resistance consequent to the presence of a $B_1$-bradykinin receptor.

3. The method of claim 2, wherein said diabetic symptoms are selected from the group consisting of hyperglycemia diuresis, proteinuria, increased nitric oxide and kallikrein urinary excretion, and said diabetic symptoms are normalized as a result of treating said mammal with said $B_1$-bradykinin receptor antagonist.

4. The method of claim 1, wherein said $B_1$-bradykinin receptor antagonist is selective for $B_1$-bradykinin receptor over $B_2$-bradykinin receptor.

5. The method of claim 1, wherein said $B_1$-bradykinin receptor antagonist is AcLys(D-βNal$^7$, Leu$^8$)desArg$^9$Bradykinin (SEQ ID NO: 22).

6. The method of claim 1, wherein said $B_1$-bradykinin receptor antagonist is selected from the group consisting of Sar(D-Tic$^7$, Leu$^8$)desArg$^9$Bradykinin (SEQ ID NO: 13)
Sar(D-Tic$^7$, Ile$^8$)desArg$^9$Bradykinin (SEQ ID NO: 39)
AcLys(D-Tic$^7$, Ile$^8$)desArg$^9$Bradykinin (SEQ ID NO: 40)
AcLys(D-Tic$^7$, Ile$^8$)desArg$^9$Bradykinin (SEQ ID NO: 17)
AcLys(D-βNal$^7$, Leu$^8$)desArg$^9$Bradykinin (SEQ ID NO: 22)
AcLys(D-βNal$^7$, Ile$^8$)desArg$^9$Bradykinin (SEQ ID NO: 23)
D-Arg(D-βNal$^7$, Ile$^8$)desArg$^9$Bradykinin (SEQ ID NO: 27)
D-Arg(D-βNal$^7$, Leu$^8$)desArg$^9$Bradykinin (SEQ ID NO: 28)
D-Lys(D-βNal$^7$, Leu$^8$)desArg$^9$Bradykinin (SEQ ID NO: 41)
D-Lys(D-βNal$^7$, Ile$^8$)desArg$^9$Bradykinin (SEQ ID NO: 29)
Sar(D-βNal$^7$, Ile$^8$)desArg$^9$Bradykinin (SEQ ID NO: 30)
Sar(D-βNal$^7$, Leu$^8$)desArg$^9$Bradykinin (SEQ ID NO: 42)
AcTyeϵAhxLys(Leu$^8$)desArg$^9$Bradykinin (SEQ ID NO:31)
AcTyeϵAhxLys(Ile$^8$)desArg$^9$Bradykinin (SEQ ID NO: 43)
SarTyeϵAhxLys(Leu$^8$)desArg$^9$Bradykinin(SEQ ID NO: 32)
SarTyeϵAhxLys(Leu$^8$)desArg$^9$Bradykinin (SEQ ID NO: 44)
SarTyeϵAhxLys(D-βNal$^7$,Ile$^8$)desArg$^9$Bradykinin (SEQ ID NO: 33)
SarTyeϵAhxLys(D-βNal$^7$, Leu$^8$)desArg$^9$Bradykinin (SEQ ID NO: 45)
SarTye(3,5-iodine)ϵAhxLys (D-βNal$^7$, Ile$^8$) desArg$^9$Bradykinin (SEQ ID NO: 34), and
SarTye(3,5-iodine)ϵAhxLys (D-βNal$^7$, Leu$^8$) desArg$^9$Bradykinin (SEQ ID NO: 46).

7. The method of claim 1, wherein said $B_1$-bradykinin receptor antagonist is AcLys(D-βNal$^7$, Ile$^8$) desArg$^9$Bradykinin (SEQ ID NO: 23).

8. A method of treating hyperalgesia in a $B_1$-bradykinin receptor mediated inflammatory condition in a mammal, said method comprising the step of administering to said mammal a therapeutically effective amount of a $B_1$-bradykinin receptor antagonist of the Formula I:

A-Arg-Pro-B-Gly-Phe-Ser-C-E (formula I, SEQ ID NO: 47 or SEQ ID NO: 48), wherein the groups A, B, C and E are independently defined and with the proviso that said $B_1$-bradykinin receptor antagonist is not SEQ ID NO:15 or SEQ ID NO: 16, wherein said $B_1$-bradykinin receptor antagonist is administered under conditions effective to ameliorate the hyperalgesia in a $B_1$-bradykinin receptor mediated inflammatory condition in said mammal.

9. The method of claim 8, wherein said $B_1$-bradykinin receptor antagonist is selected from the group consisting of:
Sar(D-TiC⁷, Leu⁸)desArg⁹Bradykinin (SEQ ID NO:13)
Sar(D-Tic⁷, Ile⁸)desArg⁹ Bradykinin (SEQ ID NO:39)
AcLys(D-Tic⁷, Ile⁸)desArg⁹ Bradykinin(SEQ ID NO:40)
D-Arg(D-Tic⁷, Ile⁸)desArg⁹ Bradykinin (SEQ ID NO: 17)
AcLys(D-βNal⁷, Leu⁸)desArg⁹ Bradykinin (SEQ ID NO:22)
AcLys(D-βNal⁷, Ile)desArg⁹ Bradykinin (SEQ ID NO: 23)
D-Arg(D-βNal⁷, Ile⁸)desArg⁹ Bradykinin (SEQ ID NO: 27)
D-Arg(D-βNal⁷, Leu⁸)desArg⁹ Bradykinin (SEQ ID NO: 28)
D-Lys(Dβ-Nal⁷, Leu⁸)desArg⁹ Bradykinin (SEQ ID NO: 41)
D-Lys(D-βNal⁷, Ile⁸)desArg⁹ Bradykinin (SEQ ID NO: 29)
Sar(D-βNal⁷, Ile⁸)desArg⁹ Bradykinin (SEQ ID NO: 30)
Sar(D-βNal⁷, Leu⁸)desArg⁹ Bradykinin (SEQ ID NO: 42)
AcTyrϵAhxLys(Leu⁸)desArg⁹ Bradykinin (SEQ ID NO: 31)
AcTyrϵAhxLys(Ile⁸)desArg⁹ Bradykinin (SEQ ID NO: 43)
SarTyrϵAhxys(Leu⁸)desArg⁹ Bradykinin (SEQ ID NO: 32)
SarTyrϵAhxys(Ile⁸)desArg⁹ Bradykinin (SEQ ID NO: 44)
SarTyrϵAhxys(D-Nal⁷, Ile⁸)desArg⁹ Bradykinin (SEQ ID NO: 33)
SarTyrϵAhxys(D-Nal⁷, Leu⁸)desArg⁹Bradykinin (SEQ ID NO: 45)
SarTyr(3,5-iodine)AhxLys(D-Nal⁷, Ile⁸)desArg⁹ Bradykinin (SEQ ID NO: 34), and
SarTyr(3,5-iodine)AhxLys(D-Nal⁷, Leu⁸)desArg⁹ Bradykinin (SEQ ID NO: 46).

10. The method of claim 8, wherein said $B_1$-bradykinin receptor antagonist is selective for $B_1$-bradykinin receptor over $B_2$-bradykinin receptor.

11. The method of claim 8, wherein said $B_1$-bradykinin receptor antagonist is AcLys(D-βNal⁷, Leu⁸)desArg⁹Bradykinin (SEQ ID NO: 22).

12. The method of any one of claims 2,3 or 4, wherein said $B_1$-bradykinin receptor antagonist is AcLys(D-βNal⁷, Ile⁸)desArg⁹Bradykinin (SEQ ID NO:23).

* * * * *

UNITED STATES PATENT AND TRADEMARK OFFICE
CERTIFICATE OF CORRECTION

PATENT NO. : 7,041,785 B1  
APPLICATION NO. : 09/242751  
DATED : May 9, 2006  
INVENTOR(S) : Regoli et al.

It is certified that error appears in the above-identified patent and that said Letters Patent is hereby corrected as shown below:

Title page, Col. 1

Item (75), Inventors: First inventor should read : Domenico Regoli, Magog (CA);

Signed and Sealed this

Twenty-first Day of November, 2006

JON W. DUDAS  
*Director of the United States Patent and Trademark Office*

SEQUENCE LISTING

<160> NUMBER OF SEQ ID NOS: 48

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
1               5

<210> SEQ ID NO 2
<211> LENGTH: 10
<212> TYPE: PRT
<213> ORGANISM: Homo sapiens

<400> SEQUENCE: 2

Lys Arg Pro Pro Gly Phe Ser Pro Phe Arg
1               5                   10

<210> SEQ ID NO 3
<211> LENGTH: 8
<212> TYPE: PRT
<213> ORGANISM: Homo sapiens

```
<400> SEQUENCE: 3

Arg Pro Pro Gly Phe Ser Pro Phe
1               5

<210> SEQ ID NO 4
<211> LENGTH: 9
<212> TYPE: PRT
<213> ORGANISM: Homo sapiens

<400> SEQUENCE: 4

Lys Arg Pro Pro Gly Phe Ser Pro Phe
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Construct

<400> SEQUENCE: 5

Arg Pro Pro Gly Phe Ser Pro Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Lys Arg Pro Pro Gly Phe Ser Pro Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa = trans-4-hydroxy-L-proline

<400> SEQUENCE: 7

Lys Arg Pro Xaa Gly Phe Ser Pro Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = trans-4-hydroxy-L-proline

<400> SEQUENCE: 8

Xaa Arg Pro Xaa Gly Phe Ser Pro Leu
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (4)..(4)
<223> OTHER INFORMATION: Xaa = trans-4-hydroxy-L-proline

<400> SEQUENCE: 9

Xaa Arg Pro Xaa Gly Phe Ser Pro Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = trans-4-hydroxy-L-proline
<220> FEATURE:
<221> NAME/KEY: MISC_FEATURE
<222> LOCATION: (8)..(8)
<223> OTHER INFORMATION: Xaa = D-Phenylalanine

<400> SEQUENCE: 10

Xaa Arg Pro Xaa Gly Phe Ser Xaa Phe
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa - D-Arginine
<220> FEATURE:
<221> NAME/KEY: MISC_FEATURE
<222> LOCATION: (4)..(4)
<223> OTHER INFORMATION: Xaa = trans-4-hydroxy-L-proline
<220> FEATURE:
<221> NAME/KEY: MISC_FEATURE
<222> LOCATION: (8)..(8)
<223> OTHER INFORMATION: Xaa = D-Phenylalanine

<400> SEQUENCE: 11

Xaa Arg Pro Xaa Gly Phe Ser Xaa Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (7)..(7)
<223> OTHER INFORMATION: Xaa = D-1,2,3,4-tetrahydroisoquilonine-
      3carboxylic acid

<400> SEQUENCE: 12

Arg Pro Pro Gly Phe Ser Xaa Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 13

Xaa Arg Pro Pro Gly Phe Ser Xaa Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 14

Lys Arg Pro Pro Gly Phe Ser Xaa Leu
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 15

Xaa Arg Pro Pro Gly Phe Ser Xaa Leu
1               5

<210> SEQ ID NO 16
<211> LENGTH: 9
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 16

Xaa Arg Pro Pro Gly Phe Ser Xaa Leu
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 17

Xaa Arg Pro Pro Gly Phe Ser Xaa Ile
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = L-(1,2,3,4-tetrahydroisoquinoline-
      3carboxylic acid)

<400> SEQUENCE: 18

Xaa Arg Pro Pro Gly Phe Ser Xaa Ile
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)
```

-continued

```
<400> SEQUENCE: 19

Xaa Arg Pro Pro Gly Phe Ser Xaa Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = trans-4-hydroxy-L-proline
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 20

Xaa Arg Pro Xaa Gly Phe Ser Xaa Phe
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = trans-4-hydroxy-L-proline
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 21

Xaa Arg Pro Xaa Gly Phe Ser Xaa Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (8)..(8)
<223> OTHER INFORMATION: Xaa = D-beta-3-(2-naphthyl)alanine

<400> SEQUENCE: 22

Xaa Arg Pro Pro Gly Phe Ser Xaa Leu
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 23

Xaa Arg Pro Pro Gly Phe Ser Xaa Ile
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (8)..(8)
<223> OTHER INFORMATION: Xaa = L-beta-3-2(naphthyl) alanine

<400> SEQUENCE: 24

Xaa Arg Pro Pro Gly Phe Ser Xaa Ile
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (7)..(7)
<223> OTHER INFORMATION: Xaa = N-methyl alanine

<400> SEQUENCE: 25

Xaa Arg Pro Pro Gly Phe Xaa Pro Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (7)..(7)
<223> OTHER INFORMATION: Xaa - N-methyl alanine
```

```
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 26

Xaa Arg Pro Pro Gly Phe Xaa Xaa Ile
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 27

Xaa Arg Pro Pro Gly Phe Ser Xaa Ile
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 28

Xaa Arg Pro Pro Gly Phe Ser Xaa Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Lysine
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 29

Xaa Arg Pro Pro Gly Phe Ser Xaa Ile
1               5

<210> SEQ ID NO 30
<211> LENGTH: 9
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 30

Xaa Arg Pro Pro Gly Phe Ser Xaa Ile
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl tyrosine
<220> FEATURE:
<221> NAME/KEY: MISC_FEATURE
<222> LOCATION: (2)..(2)
<223> OTHER INFORMATION: Xaa = Epsilon-aminohexanoic acid

<400> SEQUENCE: 31

Xaa Xaa Lys Arg Pro Pro Gly Phe Ser Pro Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (3)..(3)
<223> OTHER INFORMATION: Xaa = Epsilon-aminohexanoic acid

<400> SEQUENCE: 32

Xaa Tyr Xaa Lys Arg Pro Pro Gly Phe Ser Pro Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (3)..(3)
<223> OTHER INFORMATION: Xaa = Epsilon-aminohexanoic acid
<220> FEATURE:
<221> NAME/KEY: MISC_FEATURE
<222> LOCATION: (11)..(11)
<223> OTHER INFORMATION: Xaa = D-beta-3-(2-naphthyl) alanine
```

-continued

```
<400> SEQUENCE: 33

Xaa Tyr Xaa Lys Arg Pro Pro Gly Phe Ser Xaa Ile
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (2)..(2)
<223> OTHER INFORMATION: Xaa = Tyrosine (3,5-iodine)
<220> FEATURE:
<221> NAME/KEY: MISC_FEATURE
<222> LOCATION: (3)..(3)
<223> OTHER INFORMATION: Xaa = Epsilon-aminohexanoic acid
<220> FEATURE:
<221> NAME/KEY: MISC_FEATURE
<222> LOCATION: (11)..(11)
<223> OTHER INFORMATION: Xaa = D-beta-3-(2-naphthyl) alanine

<400> SEQUENCE: 34

Xaa Xaa Xaa Lys Arg Pro Pro Gly Phe Ser Xaa Ile
1               5                   10

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = Trans-4-hydroxy-L-proline
<220> FEATURE:
<221> NAME/KEY: MISC_FEATURE
<222> LOCATION: (6)..(6)
<223> OTHER INFORMATION: Xaa = p-(2-thienyl) L-alanine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)
<220> FEATURE:
<221> NAME/KEY: MISC_FEATURE
<222> LOCATION: (9)..(9)
<223> OTHER INFORMATION: Xaa = L-(3aS,7aS)-octahydro-indol-2-carboxylic
      acid

<400> SEQUENCE: 35

Xaa Arg Pro Xaa Gly Xaa Ser Xaa Xaa
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (3)..(3)
<223> OTHER INFORMATION: Xaa = Trans-4-hydroxy-L-proline
<220> FEATURE:
<221> NAME/KEY: MISC_FEATURE
<222> LOCATION: (5)..(5)
<223> OTHER INFORMATION: Xaa = p-(2-thienyl) L-alanine
<220> FEATURE:
<221> NAME/KEY: MISC_FEATURE
<222> LOCATION: (7)..(7)
<223> OTHER INFORMATION: Xaa = D-(1,2,3,4-tetrahydroisoquinoline-
      3carboxylic acid)
<220> FEATURE:
<221> NAME/KEY: MISC_FEATURE
<222> LOCATION: (8)..(8)
<223> OTHER INFORMATION: Xaa = L-(3aS,7aS)-octahydro-indol-2-carboxylic
      acid

<400> SEQUENCE: 36

Arg Pro Xaa Gly Xaa Ser Xaa Xaa
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = Trans-4-hydroxy-L-proline
<220> FEATURE:
<221> NAME/KEY: MISC_FEATURE
<222> LOCATION: (8)..(8)
<223> OTHER INFORMATION: Xaa = D-trans-4-hydroxy-L-proline (trans
      propyl)
<220> FEATURE:
<221> NAME/KEY: MISC_FEATURE
<222> LOCATION: (9)..(9)
<223> OTHER INFORMATION: Xaa = L-(3aS,7aS)-octahydro-indol-2-carboxylic
      acid

<400> SEQUENCE: 37

Xaa Arg Pro Xaa Gly Phe Ser Xaa Xaa
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Arginine
<220> FEATURE:
<221> NAME/KEY: MISC_FEATURE
<222> LOCATION: (4)..(4)
<223> OTHER INFORMATION: Xaa = Trans-4-hydroxy-L-proline
<220> FEATURE:
<221> NAME/KEY: MISC_FEATURE
<222> LOCATION: (8)..(8)
<223> OTHER INFORMATION: Xaa = D-trans-4-hydroxy-L-proline (trans
      thiophenyl)
```

```
<220> FEATURE:
<221> NAME/KEY: MISC_FEATURE
<222> LOCATION: (9)..(9)
<223> OTHER INFORMATION: Xaa = L-(3aS,7aS)-octahydro-indol-2-carboxylic
      acid

<400> SEQUENCE: 38

Xaa Arg Pro Xaa Gly Phe Ser Xaa Xaa
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosnine (N-methyl-glycine)
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 39

Xaa Arg Pro Pro Gly Phe Ser Xaa Ile
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl lysine
<220> FEATURE:
<221> NAME/KEY: MISC_FEATURE
<222> LOCATION: (8)..(8)
<223> OTHER INFORMATION: Xaa = D-(1,2,3,4-tetrahydroisoquinoline-
      3carboxylic acid)

<400> SEQUENCE: 40

Xaa Arg Pro Pro Gly Phe Ser Xaa Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = D-Lysine
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 41

Xaa Arg Pro Pro Gly Phe Ser Xaa Leu
1               5
```

```
<210> SEQ ID NO 42
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (8)..(8)
<223> OTHER INFORMATION: Xaa = D-beta-3-(2-naphthyl) alanine

<400> SEQUENCE: 42

Xaa Arg Pro Pro Gly Phe Ser Xaa Leu
1               5

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Acetyl tyrosine
<220> FEATURE:
<221> NAME/KEY: MISC_FEATURE
<222> LOCATION: (2)..(2)
<223> OTHER INFORMATION: Xaa = Epsilon-aminohexanoic acid

<400> SEQUENCE: 43

Xaa Xaa Lys Arg Pro Pro Gly Phe Ser Pro Ile
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (3)..(3)
<223> OTHER INFORMATION: Xaa = Epsilon-aminohexanoic acid

<400> SEQUENCE: 44

Xaa Tyr Xaa Lys Arg Pro Pro Gly Phe Ser Pro Ile
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (3)..(3)
<223> OTHER INFORMATION: Xaa = Epsilon-aminohexanoic acid
```

<220> FEATURE:
<221> NAME/KEY: MISC_FEATURE
<222> LOCATION: (11)..(11)
<223> OTHER INFORMATION: Xaa = D-beta-3-(2-naphthyl) alanine

<400> SEQUENCE: 45

Xaa Tyr Xaa Lys Arg Pro Pro Gly Phe Ser Xaa Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa = Sarcosine (N-methyl-glycine)
<220> FEATURE:
<221> NAME/KEY: MISC_FEATURE
<222> LOCATION: (2)..(2)
<223> OTHER INFORMATION: Xaa = Tyrosine (3,5-iodine)
<220> FEATURE:
<221> NAME/KEY: MISC_FEATURE
<222> LOCATION: (3)..(3)
<223> OTHER INFORMATION: Xaa = Aminohexanoic acid
<220> FEATURE:
<221> NAME/KEY: MISC_FEATURE
<222> LOCATION: (11)..(11)
<223> OTHER INFORMATION: Xaa = D-beta-3-(2-naphthyl) alanine

<400> SEQUENCE: 46

Xaa Xaa Xaa Lys Arg Pro Pro Gly Phe Ser Xaa Leu
1               5                   10

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is selected from D-arginyl, Acetyl lysyl,
    D-Lysyl, Sarcosyl, Acetyl Tyrosyl epsilon-aminohexanoyl lysyl,
    sarcosyl tyrosyl epsilon-aminohexanoyl lysyl, and sarcosyl
    tyrosyl (3,5-iodine) epsilon-aminohexanoyl lysyl
<220> FEATURE:
<221> NAME/KEY: MISC_FEATURE
<222> LOCATION: (4)..(4)
<223> OTHER INFORMATION: Xaa is selected from prolyl and hydroxyprolyl
<220> FEATURE:
<221> NAME/KEY: MISC_FEATURE
<222> LOCATION: (8)..(8)
<223> OTHER INFORMATION: Xaa is selected from D-1,2,3,4,-
    tetrahydroisoquinoline-3-carboxyl and "D-beta-(2-naphthyl) alanyl.
<220> FEATURE:
<221> NAME/KEY: MISC_FEATURE
<222> LOCATION: (9)..(9)
<223> OTHER INFORMATION: Xaa is selected from leucine and isoleucine

<400> SEQUENCE: 47

Xaa Arg Pro Xaa Gly Phe Ser Xaa Xaa
1               5

<210> SEQ ID NO 48
<211> LENGTH: 9
<212> TYPE: PRT
<213> ORGANISM: Artificial Sequence -continued

```
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is selected from Acetyl Tyrosyl epsilon-
      aminohexanoyl lysyl, sarcodyl tyrosyl epsilon-aminohexanoyl lysyl
      and sarcosyl tyrosyl (3,5-iodine) epsilon-aminohexanoyl lysyl.
<220> FEATURE:
<221> NAME/KEY: MISC_FEATURE
<222> LOCATION: (4)..(4)
<223> OTHER INFORMATION: Xaa is selected from prolyl and hydroxyprolyl.
<220> FEATURE:
<221> NAME/KEY: MISC_FEATURE
<222> LOCATION: (8)..(8)
<223> OTHER INFORMATION: Xaa = prolyl
<220> FEATURE:
<221> NAME/KEY: MISC_FEATURE
<222> LOCATION: (9)..(9)
<223> OTHER INFORMATION: Xaa is selected from leucine and isoleucine.

<400> SEQUENCE: 48

Xaa Arg Pro Xaa Gly Phe Ser Xaa Xaa
1               5
```